(12) United States Patent
D'Amato

(10) Patent No.: US 6,420,414 B1
(45) Date of Patent: *Jul. 16, 2002

(54) AMINO DERIVATIVES OF EM-138 AND METHODS OF TREATING ANGIOGENESIS WITH SAME

(75) Inventor: Robert D'Amato, Lancaster, PA (US)

(73) Assignee: The Children's Medical Center Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/710,533

(22) Filed: Nov. 9, 2000

Related U.S. Application Data

(63) Continuation of application No. 09/545,139, filed on Apr. 7, 2000, which is a division of application No. 08/950,673, filed on Oct. 16, 1997, now Pat. No. 6,071,948, which is a continuation of application No. 08/468,792, filed on Jun. 6, 1995, now Pat. No. 5,712,291, which is a continuation of application No. 08/168,817, filed on Dec. 15, 1993, now Pat. No. 5,629,327, which is a continuation-in-part of application No. 08/025,046, filed on Mar. 1, 1993, now abandoned.

(51) Int. Cl.[7] .................. A61K 31/4015; C07D 209/46
(52) U.S. Cl. ....................................... 514/416; 548/472
(58) Field of Search ........................... 514/416; 548/472

(56) References Cited

U.S. PATENT DOCUMENTS

| | | | |
|---|---|---|---|
| 2,830,991 A | 4/1958 | Keller et al. ................. | 260/281 |
| 3,560,495 A | 2/1971 | Frankus .................... | 260/247.1 |
| 3,563,986 A | 2/1971 | Frankus .................... | 260/247.1 |
| 3,625,946 A | 12/1971 | Heinrich et al. ............. | 260/281 |
| 3,705,162 A | 12/1972 | Graudums et al. .......... | 260/281 |
| 4,552,888 A | 11/1985 | Koppel et al. ............... | 514/474 |
| 4,994,443 A | 2/1991 | Folkman et al. ............... | 514/56 |
| 5,001,116 A | 3/1991 | Folkman et al. ............... | 514/56 |
| 5,021,404 A | 6/1991 | Folkman et al. ............... | 514/26 |
| 5,134,127 A | 7/1992 | Stella et al. .................... | 514/58 |
| 5,385,901 A | 1/1995 | Kaplan et al. ............ | 514/231.5 |
| 5,399,363 A | 3/1995 | Liversidge et al. ......... | 424/490 |
| 5,405,851 A * | 4/1995 | Pendergast et al. ......... | 514/267 |
| 5,405,855 A | 4/1995 | Andrulis, Jr. ................ | 514/323 |
| 5,434,170 A | 7/1995 | Andrulis, Jr. ................ | 514/323 |
| 5,443,824 A | 8/1995 | Piacquadio .............. | 424/78.02 |
| 5,502,066 A | 3/1996 | Heinemann ................. | 514/360 |
| 5,605,684 A | 2/1997 | Piacquadio .............. | 424/78.02 |
| 5,605,914 A | 2/1997 | Muller ....................... | 514/339 |

(List continued on next page.)

FOREIGN PATENT DOCUMENTS

| | | |
|---|---|---|
| AT | 1182709 | 3/1970 |
| EP | 0325199 | 7/1989 |
| EP | 0357061 | 3/1990 |
| JP | 58-131978 | 8/1983 |
| JP | 63-119500 | 5/1988 |
| WO | WO 91/10424 | 7/1991 |
| WO | WO 92/14455 | 9/1992 |

(List continued on next page.)

OTHER PUBLICATIONS

Pendergast et al., Chemical Abstracts, vol. 123:842443, 1995.*
Muller et al., Chemical Abstracts, vol. 133:252302, 2000.*
Algire, G. H., "Vascular Reactions of Normal and Malignant tissues In Vivo. I. Vascular Reactions of Mice to Wounds and to Normal and Neoplastic Transplants", *J. Nat'l Canc. Inst.*, pp. 73–85 (1945).
Allegri, A., "Confermata l'inefficacia della Talidomide Nella Terapia dei Tumori", *Gazzetta Medica Italiana*, pp. 124–127 (1964).
Ambs, S. et al., "Interactive Effects of Nitric Oxide and the p53 Tumor Suppressor Gene in Carcinogenesis and Tumor Progression", *The FASEB Journal*, vol. 11, pp. 443–448 (1997).
Apt, W. "Effect of Thalidomide on the Course of Experimental Chagas' Disease", *BOI. Chil. Parasitol*, vol. 20, No. 3, pp. 84–86 (1965).
Aronson, et al., "Thalidomide–Induced Peripheral Neuropathy. Effect of Serum Factor on Nerve Cultures", *Arch. Dermatol.*, vol. 120, No. 11, pp. 1466–1470 (1984).
Bach, et al., "Studies on the Possible Anti–Neoplastic Effect of Thalidomide", *ACTA Pathologica et Microbiologica Scandinavia*, vol.59, pp. 491–499 (1963).
Bach, et al., "Thalidomide in Cancer Chemotherapy", *The Lancet*, vol. 1, p. 1271 (1963).
Bahmer, F.A., "Therapie bel lymphozytischer Infiltration", *Der Hautarzt*, vol. 43, p. 663 (1992).
Balabanova, et al., "Lupus Erythermatosus Hypertrophicus et Produndus", *Z. Hautkr.*, vol. 67, No. 9, pp. 812–815 (1992).
Barnes, et al., "Tumor Necrosis Factor Production in Patients with Leprosy", *Infection and Immunity*, vol. 60, No. 4, pp. 1441–1446 (1992).
Barnhill, et al., "Thalidomide: Use and Possible Mode of Action in Reactional Lepromatous Leprosy and in Various Other Conditions",*J. Am. Acad. Dermatol.*, vol. 7, No. 3, pp. 317–323 (1982).
Barnhill, R. et al., "Studies on the Anti–inflammatory Properties of Thalidomide: Effects on Polymorphonuclear Leukocytes and Monocytes", *J. Am. Acad. Derm.*, vol. 11, No. 5, Part 1, pp. 814–819 (1984).
Barriere, H., "Traitement par la thalidomide", *La Presse Médicale*, vol. 12, No. 15, pp. 963 (1983).
Bazzoli, et al., "The Effects of Thalidomide and Two Analogues on the Regenerating Forelimb of the Newt", *J. Embryol. Exp. Morph.*, vol. 41, pp. 125–135 (1977).

(List continued on next page.)

*Primary Examiner*—Richard L. Raymond
(74) *Attorney, Agent, or Firm*—Kilpatrick Stockton LLP

(57) ABSTRACT

The present invention comprises a group of compounds that effectively inhibit angiogenesis. More specifically, thalidomide and various related compounds such as thalidomide precursors, analogs, metabolites and hydrolysis products have been shown to inhibit angiogenesis and to treat disease states resulting from angiogenesis. Importantly, these compounds can be administered orally.

52 Claims, 5 Drawing Sheets

U.S. PATENT DOCUMENTS

| | | | | |
|---|---|---|---|---|
| 5,643,915 A | | 7/1997 | Andrulis, Jr. et al. | 514/279 |
| 5,654,312 A | | 8/1997 | Andrulis, Jr. et al. | 514/279 |
| 5,679,696 A | | 10/1997 | Fenton et al. | 514/354 |
| 5,712,291 A | * | 1/1998 | D'Amato | 514/323 |
| 5,731,325 A | | 3/1998 | Andrulis, Jr. et al. | 514/323 |
| 6,071,948 A | * | 6/2000 | D'Amato | 514/416 |

FOREIGN PATENT DOCUMENTS

| | | |
|---|---|---|
| WO | WO 92/18496 | 10/1992 |
| WO | WO 94/20085 | 9/1994 |
| WO | WO 95/04533 | 2/1995 |
| WO | WO 00/55134 | 9/2000 |

OTHER PUBLICATIONS

Beck, Jr. et al. "Vascular Development: Cellular and Molecular Regulation", *The FASEB Journal*, vol. 11, pp. 365–374 (1997).

Beccerica, E., "L'approccio terapeutico al paziente anziano con artrite reumatoide", *Clin. Ter.*, vol. 122, pp. 289–298 (1987).

Belaube, P. et al., "Should Thalidomide be Rehabilitated?", *Sem. Hop. Paris*, vol. 59, No. 45, pp. 3101–3104 (1983).

Bensinger, W.I., "Supportive Care in Marrow Transplantation", *Curr. Opin. Oncol.*, vol. 4, No. 4, pp. 614–623 (1992).

Bernal, et al., "Cellular Immune Effects of Thalidomide in Actinic Prurigo", *Int'l. J. of Dermat.*, vol. 31, No. 8, pp. 599–600 (1992).

Blair, R. et al., "Human Mast Cells Stimulate Vaccine Tube Formation", *Journal of Clinical Investigation*, vol. 99, No. 11, pp, 2691–2700 (1997).

Blaschke, V. et al., Chromatographische Racemattreunnung von Thalidomid und teratogene Wirkung der Enantiomere, *Arzneimittel Forsch./Drug Res.*, vol. 29, No. II, pp. 1640–1642 (1979).

Bonifacino, J. et al., "A Peptide Sequence Confers Retention and Rapid Degradation in the Endoplasmic Reticulum", *Science*, vol. 2, pp. 79–80 (1990).

Bonnetblanc, et al., "Thalidomide and Recurrent Aphthous Stomatitis: a Follow–up Study", *Dermatology*, vol. 193, No. 4, pp. 321–323 (1996).

Boodman, S.G., "Questions About a Popular Prenatal Test", *The Washington Post* (1992).

Bowers, et al., "Effect of Thalidomide on Orogenital Ulceration", *Br. Med. Journ.*, vol. 287, No. 6395, pp. 799–800 (1983).

Boylen, J.B. et al., "Teratogenic Effects of Thalidomide and its Metabolites on the Developing Chick Embryo", *Canadian Journal of Biochemistry*, vol. 42, pp. 35–42 (1964).

Braun, et al., "Thalidomide Metabolite Inhibits Tumor Cell Attachment to Concanavalin a Coated Surfaces", *Biochem. Biophys. Res. Comm.*, vol. 98, No. 4, pp. 1029–1034 (1981).

Brem, H. et al., "Interstitial Chemotherapy with Drug Polymer Implants for the Treatment of Recurrent Gliomas", *J. Neurosurg.*, vol. 74, pp. 441–446 (1991).

Bressler, S. et al., "Clincopathologic Correlation of Occult Choroidal Neovascularization in Age–Related Macular Degeneration", *Arch. Ophthalmol.*, vol. 110, p. 827 (1992).

Brodhagen, H., "Significant Response of Oral Aphthosis to Thalidomide Treatment", *J. Am. Acad. Dermatol.*, vol. 13, No. 3, p. 509 (1985).

Brovarone, et al., "Occhio e gravidanza", *Minerva Ginecol.*, vol. 43, pp. 141–167 (1991).

Browne, M.J. et al., Expression of Recombinant Human Plasminogen and Aglycoplasminogen in HeLa Cells, *Fibrinolysis*, vol. 5, pp. 257–260 (1991).

Bubl, et al., "Dysphagia in Dermatologic Disease", *Dysphagia*, vol. 8, No. 2, pp. 85–90 (1993).

Buckley, C. et al., "Pyoderma Gangrenosum with Severe Pharyngeal Ulceration", *J. of Royal Society of Medicine*, vol. 83, pp. 590, 591 (1990).

Buelens, I., Treatment of a Grade II Astrocytoma with Thalidomide (Phthalylglutamic Acid Imide) [Behandlung eines Astrocytoms II. Grades mit Thaliodmid (N–Phthalyl-glutaminsäureimid)], *Arzneim–Forsch.*, vol. 17, No. 5, pp. 646–648 (1967).

Bullock, W.E., "The Clinical Significance of Erythema Nodosum", *Hosp. Pract.*, vol. 21, No. 3, pp. 102E–2H, 102K–2L, 102Q–2R pas (1986).

Burger, et al., "Epidermolysis Bullosa Acquisita, a Rare Late Complication of Allogeneicbone Marrow Transplantation?", *Bone Marrow Transplant*, vol. 9, No. 2, pp. 139–141 (1992).

Burrows, N.P., "Thalidomide Modifies Disease", *Brit. Med. J.*, vol. 307, No. 6909, pp. 939–940 (1993).

Calnan, et al., "Actinic Prurigo (Hutchinson's Summer Prurigo)", *Clin. Exp. Dermatol.*, vol. 2, No. 4, pp. 365–372 (1977).

Cant, J.S., "Minor Ocular Abnormalities Associated With Thalidomide", *The Lancet*, p. 1134 (1966).

Carmichael, et al., "Thalidomide: A Restricted Role", *Lancet*, vol. 339, No. 8805, p. 1362 (1992).

Cashin, C.H. et al., "Angiogenesis and Chronic Inflammation", *Agents and Actions*, vol. 34, No. 3/4, pp. 332–338 (1991).

Casini, G. et al., "Preparazione Di Uno Degli Antipodi Ottici Della 2–Ftalimmidoglutarimmide", *Il Pharmaco, Ed. Sc.*, vol. XIX, Fasc. 6, pp. 563–565 (1964).

Caswell, L.R. et al., "Nitrophthaloyl and aminophthaloyl derivatives of amino acids", J. Chem. Eng. Data, vol. 13, No. 2, pp. 291–292 (1968) (Abstract only).

Chapon, et al., "Neuropathies Caused by Thalidomide", *Rev. Neurol.*, vol. 141, No. 11, pp. 719–728 (1985).

Chaudhry, A. et al., "Effects of Prednisolone and Thalidomide on Induced Submandibular Gland tumors in Hampsters", *Canc. Res.*, vol. 26, No. 9, Part 1, pp. 1884–1886 (1966).

Chen, T. et al., "Plasma Pharmacokinetics and Urinary Excretion of Thalidomide after Oral Dosing in Healthy Male Volunteers", *The Am. Society for Pharma. and Experi. Therapeutics*, vol. 17, No. 4, pp. 402–405 (1988).

Chosidow, O, et al., "Sclerodermatous Chronic Graft–Versus–Host Disease: Analysis of Sevencases", *J. Am. Acad. Dermatol.*, vol. 26, No. 1, pp. 49–55 (1992).

Claydon, et al., "Gastrointestinal Emergencies in HIV Infection", *Balliere's Clin Gastroennterol.*, vol. 5, No. 4, pp. 887–911 (1991).

Clemmensen, et al., "Thalidomide Neurotoxicity", *Arch. Dermatol*, vol. 120, No. 3, pp. 338–341 (1984).

Colville–Nash, P.R. et al., "Angiogenesis and rheumatoid arthritis: Pathogenic and Therapeutic Implications", *Ann. Rheum. Dis.*, vol. 51, pp. 919–925 (1992).

Congy, et al., "Plasma Zinc Levels in Elderly Patients Hospitalized in Long Stay Units. Correlations with Other Nutritional Markers, Immunological Tests and Survival", *Sem. Hop. Paris,* vol. 59, No. 45, pp. 3105–3108 (1983).

Costa, et al., "Aseptic Adenitis in a Patient with *Pyoderma Gangrenosum*", *Ann. Dermatol.,* vol. 121, No. 8, pp. 550–552 (1994) (Abstract Only).

Crain, E. et al., "The Effect of Thalidomide on Experimental Autoimmune Myasthenia Gravis", *J. of Autoimmunity,* vol. 2, pp. 197–202 (1989).

Crawford, C.L., "Letter: Thalidomide in Erythema Nodosum Leprosum", *Lancet,* vol. 2, No. 839, pp. 1201–1202 (1973).

Crawford, C.L., "Treatment of Erythema Nodosum Leprosum with Thalidomide", *Lancet,* vol. 2, No. 828, pp. 567–568 (1973).

Crawford, C.L., "Use of Thalidomide in Leprosy [letter; comment]", *BMJ,* vol. 302, No. 6729, pp. 1603–1604 (1991).

Crum, et al., "A New Class of Steroids Inhibits Angiogenesis in the Presence of Heparin or a Heparin Fragment", *Science,* vol. 230, pp. 1375–1378 (1985).

Current Bibliographics in Medicine, "Thalidomide: Potential Benefits and Risks", *National Inst. Health, National Library of Medicine,* pp. 1–72 (Jan. 1963–Jul. 1997).

Dark et al., "Combretastin A–4, an Agent that Displays Potent and Selective Toxicity Toward Tumor Vasculature", *Cancer Research,* vol. 37, pp. 1829–1834 (1997).

David–Bajar, K.M., "Subacute Cutaneous Lupus Erythematosus", *J. Invest. Dermatol.* vol. 100, No. 1, pp. 2S–8s (1993).

D'Amato, R. J. et al., "Thalidomide is an Inhibitor of Angiogenesis", *Proc. Natl. Acad. Sci.,* vol. 91, pp. 4082–4085 (1994).

D'Amato, et al., "Angiogenesis Inhibition in Age–Related Macular Degeneration", *Ophthalmology,* vol. 102, No. 9, pp. 1261–1262 (1995).

D'Amato, et al., "Microscopic Analysis of Retinal–Vessels Utilizing Fluorescein–Labeled High–Molecular–Weight Dextrans", *Invest. Ophthalmol. & Visual Science,* vol. 33, No. 4, p. 1082 (1992).

De, A.U. et al., "Possible Antineoplastic Agents I", *J. of Pharma. Sci.,* vol. 64, No. 2, pp. 262–266 (1975).

De, A.U. et al., "Possible Antineoplastic agents. III. Synthesis of 6–alkyl–2–[4'–methoxyphthalimido]and 6–alkyl–3–[3'–4'–dimethoxyphenyl]glutarimides", J. Indian Chem. Soc., vol. 53, No. 11, pp. 1122–1125 (1976).

De, A.U. et al., "Possible Antineoplastic Agents: Part IV–Synthesis & Antineoplastic Potency of N–Substituted □–(4,5–Dimethoxyphthalimodo)glutarimides and N–Substituted □–(4–Bromophenyl)glutarimides", Indian J. of Chemistry, vol. 16B, pp. 510–512, (Jun. 1978).

De Cock, K., "Treatment of Ulcerative Colitis", *Brit. Med. J.,* vol. 1, pp. 1356 (1979).

DeKlerk, et al., "New Methods of Treatment for Renal Allotransplants Using the Baboon as a Primate Experimental Model", *J. Urol.* vol. 102, No. 5, pp. 532–540 (1969).

Dhodapkar, et al., "A Phase II Pilot Study of Anti–Angiogenesis Therapy Using Thalidomide in Patients with Multiple Myeloma", *UARK 98–003,* pp. 1–15, date unknown.

Dicken, C. H. "Malignant pyoderma", *J. of the Am. Acad. of Dermatol.,* vol. 13, No. 6, pp. 1021–1025 (1985).

DiPaolo et al., "Thalidomide: Effects on Ehrlich Ascites Tumor Cells in vitro", *Science,* vol. 144, pp. 1583 (1964).

DiPaolo, "Effect of Thalidomide on a Variety of Transplantable Tumors", *Cancer Chemo. Reports,* vol. 29, pp. 99–102 (1963).

DiPaolo, "In Vitro Test Systems for Cancer Chemotheraphy. II. Correlation of In Vitro Inhibition of Dehydrogenase and Growth with In Vivo Inhibition of Ehrlich Ascites Tumor", *P.S.E.B.M.,* vol. 114, pp. 384–387 (1963).

DiPaolo et al., "Teratogenesis–oncogenesis: A Study of Possible Relationships", *Arch. Path.,* vol. 81, pp. 3–23 (1966).

Dorveaux, et al., "Le Traitement Actuell du Lupus Erythemateau Chronique", *Le Concouors Med.* vol. 106, No. 31, pp. 2957–2961 (1984).

Doutre, et al., "*Pyoderma Gangrenosum* and Hemopathies. A propos of 2 Cases", *Nouv Rev Fr Hematol,* vol. 29, No. 4, pp. 251–254 (1987).

Dunn, et al., "Bone Marrow Transplantation and Cataract Development", *Arch. Ophthalmol.* vol. 111, No. 10, pp. 1367–1373 (1993).

(Editorial) "Thalidomide in Dermatology and Leprosy", *Lancet,* vol. 2, No. 8446, pp. 80–81 (1985).

(Editorial) "Thalidomide Tested for Treatment of AIDS", *U.S. Pharm.,* vol. 18, No. 8, p. 14 (1993).

Eger, K. et al., "Synthesis, Central Nervous System Activity and Teratogenicity of a Homothalidomide", *Arzheim. Forsch/Drug Res.,* vol. 40 (II), No. 10, pp. 1073–1075 (1990).

Ehrlich, G.E. "Behcet's Disease: Current Concepts", *Comprehensive Therapy,* vol. 15, No. 1, pp. 27–30 (1989).

El–Naggar, A.M., et al., "Synthesis of Biologically Active 3,5–dinitrophthaloyl– and 3,5–diaminophthaloyl–amino acids and dipeptide derivatives", Indian J. Chem., Sect. B (1981) pp. 514–517, abstract only.

Elia, et al., "Giant Esophageal Ulcer Treated with Steroids in AIDS Patient(2)", *J. Acquired Immune Defic. Syndr.,* vol. 5, No. 8, pp. 848–849 (1992).

Eisenbud, L. et al., "Recurrent Aphthous Stomatitis of the Behcet's Type: Successful Treatment with Thalidomide", *Oral Surgery, Oral Medicine, Oral Pathology,* vol. 64, No. 3, pp. 289–292 (1987).

Eravelly, J. et al., "Thalidomide in Weber–Christian Disease", *The Lancet,* vol. 1, No. 8005, p. 251 (1977).

Eriksson, et al., "Drug Exposure and Flow Cytometry Analyses in a Thalidomide Treatment Schedule that Prolongs Rat Cardiac Graft Survival", *Transplant Proc.,* vol. 24, No. 6, pp. 2560–2561 (1992).

Eriksson, S. O. et al., "Synthesis and Alkaline Hydrolysis of Some N–substituted Phthalimides", *Acta Pharm. Suecica,* vol. 10, pp. 63–74 (1973).

Fabro, S. et al., "The Metabolism of Thalidomide: Some Biological Effects of Thalidomide and its Metabolites", *Brit. J. Pharmacol.,* vol. 25, pp. 352–362 (1965).

Fabro, S. et al., "Teratogenic Activity of Thalidomide and Related Compounds", *Life Sci.,* vol. 3, pp. 987–992 (1964).

Fabro, S. M.D., "Biochemical Basis of Thalidomide Teratogenicity", *The Biochemical Basis of Chemical Teratogenesis,* Chapter 5, pp. 159–178 (1981).

Fajardo, et al., "Dual Role of Tumor Necrosis Factor–α in Angiogenesis", *Am. J. Pathol.,* vol. 140, No. 3, pp. 539–544 (1992).

Faure, et al., "PMN Leukocytes Chemotaxis: Inhibition by Thalidomide", *Pathol. Biol. (Paris),* vol. 29, No. 10, pp. 601–604 (1981).

Faure, et al., "Inhibition of PMN Leukocytes Chemotaxis by Thalidomide", *Arch. Dermatol. Res.*, vol. 269, No. 3, pp. 275–280 (1980).

Fazal, N. et al., "Effect of Blocking TNF–□ on Intracellular BCG (*Bacillus Calmette Guerin*) Growth in Human Monocyte–Derived Macrophages", *FEMS Microbiology Immunology*, vol. 105, pp. 337–346 (1992).

Fickentscher, K. et al., "Stereochemical Properties and Teratogenic Activity of Some etrahydrophthalimides", *Mol. Pharmacol.*, vol. 13, pp. 133–141 (1977).

Field, E. O. et al., "Effect of Thalidomide on Splenomegaly (GVH Reaction) in the Chick Embryo. Treatment of Donor Cells Only", *Nature*, vol. 211, No. 5055, pp. 1309–1310 (1966).

Flohe, L. et al., "Studies on the Hypothetical Relationship of Thalidomide–induced Embryopathy and Collagen Biosynthesis", *Arzneimittel/Forschung (Germany West)*, vol. 31, No. 2, pp. 315–320 (1981).

Folkman, J. et al., "Angiogenesis", *J. Biol. Chem.*, vol. 267, No. 16, pp. 10931–10934 (1992).

Folkman, J. et al., "Angiogenesis Inhibition and Tumor Regression Caused by Heparin or a Heparin Fragment in the Presence of Cortisone", *Science*, vol. 221, pp. 719–725 (1983).

Folkman, J. et al., "Induction of Angiogenesis During the Transition from Hyperplasia to Neoplasia", *Nature*, vol. 339, pp. 58–61 (1989).

Folkman, J. et al., "Tumor Behavior in Isolated Perfused Organs: In Vitro Growth and Metastases of Biopsy material in Rabbit Thyroid and Canine Intestinal Segment", *Anals of Surgery*, pp. 491–502 (1966).

Folkman, J., "Tumor Angiogenesis: Therapeutic Implications", *The New England J. of Med.*, vol. 285, No. 21, pp. 1182–1186, (1971).

Folkman, J., "Angiogenesis and Its Inhibitors", *Important Advances in Oncology*, J.B. Lippincott H. Company, pp. 42–62 (1985).

Folkman, J., "Angiogenesis in Cancer, Vascular, Rheumatoid and Other Disease", *Nature Medicine*, vol. 1, No. 1, pp. 27–30 (1995).

Folkman, J., "What is the Evidence that Tumors are Angiogenesis Dependent?", *J. Naat' Cancer Inst.*, vol. 82, No. 1 (1990).

Francois, J., "Embryological Pigment Epithelial Dystrophies", *Ophthalmologica*, vol. 172, pp. 417–433 (1976).

Fuller, et al., "Thalidomide, Peripheral Neuropathy and AIDS", *Int. J. STD AIDS*, vol. 2, No. 5, pp. 369–370 (1991).

Furner., B.B., "Treatment of Subacute Cutaneous Lupus Eryhthematosus", *Int. J. Dermatol.*, vol. 29, No. 8, pp. 542–547 (1990).

Gad, et al., "Thalidomide Induces Imbalances in T–Lymphocyte Sub–Populations in the Circulating Blood of Healthy Males", *Lepr. Rev.*, vol. 56, No. 1, pp. 35–39 (1985).

Gaetani, M., "Studi Sull' Attivita Antitumorale Della Talidomide", *Giornale Italiano diu Chemioterapia*, pp. 83–86, date unknown.

Gehanno, et al., "Mouth and Pharyngeal Hyperalgesic Syndromes In AIDS", *Ann. Otolarygol Chir. Cervicofac*, vol. 107, No. 5, pp. 311–313 (1990).

Genvo, et al., "Treatment of Aphthosis with Thalidomide and with Colchicine", *Dermatologica*, vol. 168, No. 4, pp. 182–188 (1984).

Geoghiou, et al.,"HIV–Associated Oesophageal Ulcers Treated with Thalidomide", *Med. J. of Australia*, vol. 152, pp. 382–383 (1990).

Gershbein, "Effect of Transplanted Tumor and Various Agents on Liver Regeneration During Pregnancy", *P.S.E.B.M.*, vol. 126, pp. 88–92 (1967).

Gershbein, L. L., "The Thalidomide Analog. EM 12, Enhances 1,2–dimethylhydrazine–induction of Rat Colon Adenocarcinomas", *Canc. Ltrs,* vol. 60, pp. 129–133 (1991).

Gershbein, L. L., "Effect of Various Agents on Liver Regeneration and Walker Tumour Growth in Partially Hepatectomized Rats", *Canc. Res.*, vol. 26, No. 9, pp. 1905–1908 (1966).

Ghigliotti, G. et al., "Thalidomide: Treatment of Choice for Aphthous Ulcers in Patients Seropositive for Human Immunodeficiency Virus", *J. of the Am. Acad. of Dermatol.*, vol. 28, No. 2, Part I, pp. 271–272 (1993).

Gimbrone, M.A. et al., "Tumor Dormancy in Vivo by Prevention of Neovasularization", *Journal of Experimental Medicine*, vol. 136, pp. 261–276 (1972).

Gimbrone, M. A. et al., "Tumor Growth and Neovascularization: An Experimental Model Using the Rabbit Cornea", *J. Nat. Canc. Instit.*, vol. 52, No. 2, pp. 413–419 (1974).

Goihman–Yahr, Mauricio et al., "Significance of Neutrophil Activation in Reactional Lepromatous Leprosy: Effects of Thalidomide in vivo and in vitro. Activation in Adjuvant Disease", *Int. Archs. Allergy Appl. Immun.*, vol. 57, pp. 317–332 (1978).

Goihman–Yahr, M., et al., "Autoimmune Diseases and Thalidomide II. Adjuvant Disease, Experimental Allergic Encephalomyelitis and Experimental Allergic Neuritis of the Rat", *Int. J. Leprosy*, vol. 42, No. 3, pp. 266–275 (1974).

Gorin, I.,et al., "Thalidomide May Cure AIDS Ulcers", *Nurs. Times*, vol. 86, No. 24, p. 10 (1990).

Gorin, I., et al., "Thalidomide in Hyperalgic Pharyngeal Ulceration of AIDS", *Lancet*, vol. 335, p. 1343 (1990).

Goulden, V., et al., "Linear Prurigo Simulating Dermatitis Artefacta in Dominant Dystrophicepidermolysis Bullosa", *Br. J. Dermatol.*, vol. 129, No. 4, pp. 443–446 (1993).

Grabstald, H. et al., ."Clinical Experiences with Thalidomide in Patients with Cancer", *Clinical Pharmacol. and Therapeutics*, vol. 6, pp. 298–302 (1965).

Grant, D.S. et al., "Scatter Factor Induces Blood Vessel Formation in vivo", *Proc. Natl. Acad. Sci.*, vol. 90, pp. 1937–1941 (1993).

Grinspan, et al., "Treatment of Aphthae with Thalidomide", *J. Am. Acad. Dermatol.*, vol. 20, No. 6, pp. 1060–1063 (1989).

Grinspan, D., "Significance Response of Oral Aphthosis to Thalidomide Treatment", *Am. Acad. of Dermatol.*, vol. 12, No. 1, Part 1, pp. 85–90 (1985).

Grosshans, E., et al, "Thalidomide Therapy for Inflammatory Dermatoses", *Int. J. Dermatol*, vol. 23, No. 9, pp. 598–602 (1984).

Guidetti, E., et al., "Richerche Sull'azione Immunodepressiva Della Talidomide e del Prednisolone in Ratti Portatori Di Neoplasie Sperimentalmente Indotte", *Cancro*, vol. 22, pp. 503–512 (1969).

Güzler, V., "Thalidomide in Human Immunodeficiency Virus (HIV) Patients. A Review of Safety Considerations", *Drug Saf*, vol. 7, No. 2, pp. 116–134 (1992).

Güzler, V., "Thalidomide—A Therapy for the Immunological Consequences of HIV Infection?", *Medical Hypotheses*, vol. 30, No. 2, pp. 105–109 (1989).

Gutiérrez–Rodriguez, O. et al., "Treatment of Refractory Rheumatoid Arthritis—The Thalidomide Experience", *The J. of Rheumatology*, vol. 16, No. 2, pp. 158–163 (1989).

Gutiérrez–Rodriguez, O. et al., "Thalidomide A Promising New Treatment for Rheumatoid Arthritis", *Arthritis & Rheumatism*, vol. 27, No. 10, pp. 1118–1121 (1984).

Haffner, M.E. M.D., "Studies Involving Orphan Products for Treating/Diagnosing Women's Diseases", *Food and Drug Law Journal*, vol. 48, pp. 205–211 (1992).

Hamza, M. M.D., "Behcet's Disease, Palmoplantar Pustulosis and HLA–B27 Treatment with Thalidomide", *Clinical and Experimental Rheumatology*, vol. 8, No. 4, p. 427 (1990).

Hamza, M.H., "Treatment of Behcet's Disease with Thalidomide", *Clinical Rheumatol.*, vol. 5, No. 3, pp. 365–371 (1986).

Handley, J. et al., "Chronic Bullous Disease of Childhood and Ulcerative Colitis", *Pediatric Dermatol.*, vol. 19, No. 3, pp. 256–258, (1993).

Handley, J. et al., "Chronic Bullous Disease of Childhood and Ulcerative Colitis", *Brit. J. of Dermatol.*, vol. 127, Supp. 40, pp. 67–68 (1992).

Harindra, et al., "Papulo–Pruritic Eruption and Giant Ulceration of the Mouth: A Difficult Clinical Feature to Treat in the Patient Infected with Humanimmunodeficiency Virus(1)", *Arch. Intern. Med.*, vol. 152, No. 9, p. 1924 (1992).

Harris, A., "Antiangiogenesis for Cancer Therapy", *Lancet*, vol. 349 (Suppl. II), pp. 13–15 (1997).

Hasper, M.F., "Chronic Cutaneous Lupus Erythematosus. Thalidomide Treatment of 11 Patients", *Arch. Dermatol.*, vol. 19, No. 10, pp. 812–815 (1983).

Hasper, M.F., et al., "Thalidomide in the Treatment of Chronic Discoid Lupus", *Acta Derm. Venereol*, vol. 62, No. 4, pp. 321–324 (1982).

Hastings, R.C., et al., "Thalidomide in the Treatment of Erythema Nodosum Leprosum. With a Note on Selected Laboratory Abnormalities in Erythema Nodosum Leprosum", *Clin. Pharmacol. Ther.*, vol. 11, No. 4, pp. 481–487 (1970).

Hatfill, S.J. et al., "Induction of Morphological Differentiation in the Human Leukemic Cell Line K562 by. Exposure to Thalidomide Metabolites", *Leukemia Res.*, vol. 15, No. 2/3, pp. 129–136 (1991).

Hayashi, S. et al., "A Synthetic Peptide for α Chemokines Inhibits the Growth of Melonoma Cell Lines", *J. Clin. Invest.*, vol. 99, No. 11, pp. 2581–2587 (1997).

Heaton, et al., "Graft–versus–Host Disease Following Liver Transplantation", *J. R. Soc. Med.*, vol. 85, No. 6, pp. 313–314 (1992).

Hellman, K. et al., Prolongation of Skin Homograft Survival by Thalidomide, *Brit. Med. J.*, vol. 2, pp. 687–689 (1965).

Helm, F.–Ch. et al., "Comparative Teratological Investigation of Compounds Structurally and Pharmacologically Related to Thalidomide", *Arzneim.–Forsch/Drug Res.*, vol. 31 (I), No. 6, pp. 941–949 (1981).

Hendler, S. S. et al., "Thalidomide for Autoimmune Disease", *Medical Hypotheses*, vol. 10, pp. 437–443 (1983).

Hendler, S.S., "Immune Modulators Thalidomide", *The Oxygen Breakthrough*, pp. 217–219, date unknown.

Heney, D. et al., "Thalidomide Treatment for Chronic Graft–Versus–Host Disease", *Brit. J. of Haematol.* vol. 78, pp. 23–27 (1991).

Heney, D., et al., "Thalidomide in the Treatment of Graft–versus–Host Disease", *Biomed. Pharmacother*, vol. 44, No. 4, pp. 199–204 (1990).

Heney, D., et al., "Thalidomide for Chronic Graft–versus––Host Disease in Children", *Lancet*, vol. 2, No. 8623, p. 1317 (1988).

Hojyo, et al., "Actinic Prurigo (9)", *Int. J. Dermatol.*, vol. 31, No. 5, pp. 372–373 (1992).

Holm, et al., "Chronic Cutaneous Lupus Erythematosus Treated with Thalidomide", *Arch. Dermatol.*, vol. 129, No. 12, pp. 1548–1550 (1993).

Hori, A. et al., "Suppression of Solid Tumor Growth by Immunoneutralizing Monoclonal Antibody against Human Basic Fibroblast Growth Factor", *Canc. Res.*, vol. 51, pp. 6180–6184 (1991).

Hu, D.E., "Inhibition of Angiogenesis in Rats by IL–1 Receptor Antagonist and Selected Cytokine Antibodies", *Inflammation*, vol. 18, pp. 45–58 (1994).

Hu, J. et al., "A Novel Regulatory Function of Proteolytically Cleaved VEGF–2 for Vascular Endothelial and Smooth Muscle Cells", *The FASEB Journal*, vol. 11, pp. 498–504 (1997).

Ingber, D. et al., "Synthetic Analogues of Fumagillin that Inhibit Angiogenesis and Suppress Tumor Growth", *Ltrs. to Nat.*, vol. 348, pp. 555–557 (1990).

Ingber, D., "Drug News and Trial Developments", *AIDS Patient Care*, vol. 6, No. 6, p. 288 (1992).

Jacobson, J. et al., "Thalidomide for the Treatment of Oral Aphthous Ulcers in Patients with Human Immunodeficiency Virus Infection", *The New England Journal of Medicine*, vol. 336, No. 21, pp. 1487–1493 (1997).

Jacobson, et al., "The Diagnosis and Treatment of Leprosy", *South Med.. J.*, vol. 60, No. 8, pp. 979–985 (1976).

Jager, et al., "Clinical Observations in the Treatment of Leprosy Reaction with Cyclic Imides", *Int. J. Lepr. Other Mycobact Dis.*, vol. 39, No. 2, p. 589 (1971).

Jeltsch, M. et al., "Hyperplasia of Lymphatic Vessels in VEGF–C Transgenic Mice", *Science*, vol. 276, pp. 1423–1426 (1997).

Jenkins, et al., "Thalidomide, Orogenital Ulcers, and Risk of Teratogenicity", *The Lancet*, vol. 1, No. 8417–18, p. 511 (1985).

Jenkins, et al., "Thalidomide in Severe Orogenital Ulceration", *The Lancet*, vol. 2, No. 8417–18, pp. 1424–1426 (1984).

Jennings, et al., "Effect of Actinomycin D on the Production of Acute Phase Protein in the Rabbit", *Experientia*, vol. 25, pp. 305–306 (1969).

Jew, et al., "Thalidomide in Erythema Nodusum Leprosum", *DICP*, vol. 24, No. 5, pp. 482–483 (1990).

Johnke, et al., "Thalidomide Treatment of Prurigo Nodularis", *Ugeskr Laeger*, vol. 155, No. 38, pp. 3028–3030 (1993) (Abstract Only).

Jönsson, N., "Chemical Structure and Teratogenic Properties IV. An Outline of a Chemical Hypothesis for the Teratogenic Action of Thalidomide", *Acia Pharm. Succica*, vol. 9, pp. 543–562 (1972).

Jösson, N., "Chemical Structure and Teratogenic Properties I. Synthesis and Teratogenic Activity in Rabbits of some Derivatives of Phthalidmide, Isoindoine–1–one, 1.2–Benzisothiazoline–3–one–1, 1–Dioxide and 4(3II)–Quinazolinone", *Acia Pharm Succica*, vol. 9, pp. 431–436 (1972).

Jönsson, N., "Chemical Structure and Teratogenic Properties III a Review of Available Data on Structure–Activity Relationships and Mechanism of Action of Thalidomide Analogues", *Acia Pharm. Succia,* vol. 9, pp. 21–542 (1972).

Jorizzo, et al., "Thalidomide Effects in Behcet's Syndrome and Pustular Vasculitis", *Arch. Intern. Med.,* vol. 146, No. 5, pp. 878–881 (1986).

Juret, et al., "Absence d'effet Carcino–Frénateur du Talidomide vis-á-vis de deux Tumerus Greffées", *Société de Biologie,* vol. 23, pp. 246–249 (1963).

Kaitin, K.I., "Graft–versus–Host Disease", *N. Engl. J. Med.,* vol. 325, No. 5, pp. 357–358 (1991).

Kaplan, G. et al., "TNF☐☐regulation of HIV1: Biology and Therapy", *Res. in Immunology,* vol. 145, No. 8–9, pp. 685–690 (1994).

Katsuta, et al., "Carcinogenesis in Tissue Culture. 3. Effects of the Second Treatments on DAB–Induced Proliferating Liver Cells of Normal Rats in Culture", *Jpn. J. Exp. Med.,* vol. 35, No. 4, pp. 231–248 (1965).

Keenan, R.J. et al., "Immunosuppressive Properties of Thalidomide", *Transplantation,* vol. 52, No. 5, pp. 908–910 (1991).

Kenyon, et al., "The Discovery of New Inhibitors of Angiogenesis Using an Improved Mouse Corneal Neovascularization Model", No. 459–367, p. S94 (Abstract only), 1994.

Kim, K. J. et al., "Inhibition of Vascular Endothelial Growth Factor–Induced Angiogenesis Suppresses Tumor Growth in vivo", *Ltrs. to Nat.,* vol. 362, pp. 841–844 (1993).

Kitamoto, Y. et al, "Vascular Endothelial Growth Factor is an Essential Molecule for Mouse Kidney Development: Glomerulogenesis and Nephrogenesis", *J. Clin. Invest.,* vol. 99, No. 10, pp. 2351–2357 (1997).

Klug, S. et al., "Embryotoxic Effects of Thalidomide Derivatives in the Non–Human Primate *Callithrix Jacchus*", *Arch. Toxicol.* vol. 68, pp. 203–205 (1994).

Knighton, D. et al., "Avascular and Vascular Phases of Tumor Growth in the Chick Embryo", *Br. J. Canc.,* vol. 35, pp. 347–356 (1977).

Knop, et al., "Thalidomide in the Treatment of Sixty Cases of Chronic Discoid Lupus Erythematosus", *Br. J. Dermatol,* vol. 108, No. 4, pp. 461–466 (1983).

Koch, H.P. et al., "4 Thalidomide and Congeners as Anti–inflammatory Agents", *Progress in Medicinal Chemistry,* vol. 22, pp. 166–242 (1985).

Korn, et al., "The Second International Workshop on Scleroderma Research", *Matrix,* vol. 13, No. 5, pp. 427–429 (1993).

Kroger, et al., "Synergistic Effects of Thalidomide and Poly (ADP–ribose) Polymerase Inhibition on Type II Collagen –Induced Arthritis in Mice", *Inflammation,* vol. 20, No. 2, pp. 203–215 (1996).

Kundu, et al., "Prurigo Nodularis in an HIV Positive Man (2)", *Genitourinary Medicine,* vol. 71, No. 2, pp. 129–130 (1995).

Kükcüoglu, N. et al., "Thalidomide in the treatment of Recurrent Necrotic Mucocutaneous Aphthae", *Brit. J. of Dermatol.,* vol. 112, No. 5, pp. 632 (1985).

Lane, et al., "Treatment of Actinic Prurigo with Intermittent Short–Course Topical 0.05% Clobetasol 17–Propionate. A Preliminary Report", *Arch. Dermatol,* vol. 126, No. 9, pp. 1211–1213 (1990).

Languillon, J., "The Effects of Thalidomide on Leprosy Reaction", *Int. J. Lepr. Other Mycobact. Dis.,* vol. 39, No. 2, pp. 590–592 (1971).

Larsson, H., "Treatment of Severe Colitis in Behcet's Syndrome with Thalidomide (CG–217)", *J. of Intern. Med.,* vol. 228, pp. 405–407 (1990).

Ledo, E., "Photodermatosis. Part I: Photobiology, Photoimmunology, and Idiopathicphotodermatoses", *Int. J. Dermatol.,* vol. 32, No. 6, pp. 387–396 (1993).

Lehner, T., et al., "Thalidomide, Orogenital Ulcers, and Risk of Teratogenesis", *The Lancet,* vol. 8423, pp. 288–289 (1985).

Lenicque, "Action of Thalidomide on the Induction of Tentacles in Regenerating *Hydra Littoralis*", *Acta. Zool.,* pp. 127–139 (1967).

Levy, et al., "Treatment of Erythema Nodosum Leprosum with Thalidomide", *The Lancet,* vol. 2, No. 824, pp. 324–325 (1973).

Lien, W. M. et al., "The Blood Supply of Experimental Liver Metastases. II. A microcirculatory Study of the Normal and Tumor Vessels of the Liver with the Use of Perfused Silicone Rubber", *Surgery,* vol. 68, No. 2, pp. 334–340 (1970).

Lo, et al., "Treatment of Discoid Lupus Erythematosus", *Int. J. Dermatol.,* vol. 28, No. 8, pp. 497–507 (1989).

Londono, F., "Thalidomide in the Treatment of Actinic Prurigo", *Int. J. Dermatol.,* vol. 12, No. 5, pp. 326–328 (1973).

Lovell, et al., "Thalidomide in Actinic Prurigo", *Br. J. Dermatol,* vol. 108, No. 4, pp. 467–471 (1983).

Lopez, J. et al., "Thalidomide as Therapy for Intestinal Chronic GVHD", *Bone Marrow Transplantation,* vol. 11, No. 3, pp. 251–252 (1993).

Louzir, B. et al., "Erythroleucemie chez un patient ayant une maladie de Behcet et traite au long cours par thalidomide", *Annales de Medecine Interne,* vol. 143, pp. 479–480 (1992).

Lueprasitsakul, W. et al., "Effect of Thalidomide on the Incidence of Iodine–Induced and Spontaneous Lymphocytic Thyroiditis and Spontaneous Diabetes Mellitus in the BB/Wor Rat", *Acta Endocrino Logica,* vol. 123, pp. 79–83 (1990).

Lüers, H., "Failure of Mutagenic Action of Thalidomide in Drosophila", *The Lancet,* vol. II, No. 7258, p. 1332 (1962).

Magana–Garcia, M., "Antimalarials for Children", *J. Am. Acad. Dermatol,* vol. 30, No. 3, p. 510 (1994).

Maione, T. E. et al., "Inhibition of Angiogenesis by Recombinant Human Platelet Factor–4 and Related Peptides", *Science,* vol. 2, pp. 77–78 (1990).

Makonkawkeyoon, S. et al., "Thalidomide Inhibits the Replication of Human Immunodeficiency virus type 1", *Proc. Natl. Acad. Sci.,* vol. 90, pp. 5974–5978 (1993).

Marin–Padilla, M. et al. "Thalidomide Induced alterations in the Blastocyst and Placenta of the Armadillo, *Dasypus Novemcinctus Mexicanus,* Including a Choriocarcinoma", *The Am. J. of Pathol.,* vol. 43, No. 6, pp. 999–1016 (1963).

Mascaro, et al., "Thalidomide in the Treatment of Recurrent, Necrotic, and Giant Mucocutaneous Aphthae and Aphthosis", *Arch. Dermt.,* vol. 115, pp. 636–637 (1979).

Matsubara, et al, "Inhibition of Human Endothelial Cell Proliferation by Gold Compounds", *J. Clin. Invest.,* vol. 79, pp. 1440–1446 (1987).

Matsuyama, T. et al., "Cytokines and HIV Infection: is AIDS a Tumor Necrosis Factor Disease?", *AIDS,* vol. 5, No. 12, pp. 1405–1417 (1991).

Mauád, "Melhoras Clínicas Obtidas em Doentes Cancerosos Avancados com Tratamento Pela Talidomida Associada a Hormônios", *Anais Paulistas Medicina e Cirurgia,* pp. 15–39 (1963).

Maurice, et al., "The Effect of Thalidomide on Arachidonic Acid Metabolism in Human Polymorphonuclear Leukocytes and Platelets", *Br. J. Dermatol.,* vol. 115, No. 6, pp. 677–680 (1986).

McCarthy, et al., "Thalidomide for the Therapy of Graft–versus–Host Disease Following Allogeneic Bone Marrow Transplantation", *Biomed. Pharmacother,* vol. 43, No. 9, pp. 693–697 (1989).

McKenna, et al., "Linear IgA Disease, Oral Ulceration and Crohn's Disease", *Br. J. Dermatol,* vol. 127, pp. 67–68 (1992).

Meza, D. et al., "Managing the Gastrointestinal Complications of AIDS", *Drug Therapy,* vol. 23, No. 11, pp. 74–83 (1993).

Miller, et al., "Zusammentreffen Einer Thalidomid–Induzierten Fehlbildung mit Einem Malignen Lymphom Hohen Malignitätsgrades", *Monatsschr. Kinderheilkd,* vol. 128, pp. 27–29 (1980).

Miller, et al., "Treatment of Chronic Erythema Nodosum Leprosum with Cyclosporine A Produces Clinical and Immunohistologic Remission", *Int. J. Lepr. Other Mycobact. Dis.,* vol. 55, No. 3, pp. 441–449 (1987).

Misery, L. et al., "Remission of Langerhans Cell Histocytosis with Thalidomide Treatment", *Clinical and Experimental Dermatol.,* vol. 18, No. 5, p. 487 (1993).

Miura, M. et al., "Potentiating Effect of Thalidomide on Methylcholanthrene Oncogenesis in Mice", *Experieentia,* vol. 26, Fasc. 3, pp. 305–306 (1970).

Miyachi, Y., "A Possible Mechanism of Action of Thalidomide on Rheumatoid Arthritis", *Arthritis and Rheuma.,* vol. 28, No. 7, p. 836 (1985).

Miyachi, et al., "Effects of Thalidomide on the Generation of Oxygen Intermediates by Zymosan–Stimulated Normal Polymorphonuclear Leukocytes", *Arch Dermatol. Res.,* vol. 274, Nos. 3–4, pp. 363–367 (1982).

Mohri, et al., "Negative Effect of Thalidomide and Relative Substances on the Growth of HeLa Cells", *Chem. Pharm. Bull.,* vol. 16, pp. 2289–2292 (1968).

Moncada, et al., "Thalidomide—Effect on T Cell Subsets as a Possible Mechanism of Action", *Int. J. Lepr. Other Mycobact. Dis.,* vol. 53, No. 2, pp. 201–205 (1985).

Montrucchio, et al., "Tumor Necrosis Factor α–Induced Angiogenesis Depends on In Situ Platelet–Activating Factor Biosynthesis", *J. Exp. Med.,* vol. 180, pp. 377–382 (1994).

Moulin, et al., "Treatment of Jessner–Kanof Disease with Thalidomide", *Ann. Dermatol Venereol,* vol. 10, No. 8, pp. 611–614 (1983).

Mshana, et al., "Thymus–Dependent Lymphocytes in Leprosy. II. Effect of Chemotherapy on T–Lymphocyte Subpopulations", *J. Clin. Immunol.,* vol. 2, No. 2, pp. 69–74 (1982).

Mückter, et al., "Thalidomide and Tumor", *Antimicrobial Agents and Chemotherapy,* pp. 531–538 (1965).

Mummery, C.L. et al., "Screening for Cytoxicity in Neuroblastoma Cells–I. Dependence of Growth Inhibition on the Presence of Serum", *Toxicology Letters,* vol. 18, pp. 201–209 (1983).

Munro, et al., "*Pyoderma Gangrenosum* Associated with Behcet's Syndrome–Response to Thalidomide", *Clin. Exp. Dermatol.,* vol. 13, No. 6, pp. 408–410 (1988).

Muthukkaruppan, Vr. et al., "Angiogenesis in the Mouse Cornea", *Science,* vol. 205, No. 28, pp. 1416–1418 (1979).

Naafs, B. et al., "Thalidomide Therapy An Open Trial", *Intl. J. of Dermatol.,* vol. 24, No. 2, pp. 131–134 (1985).

Naafs, B., Bangkok Workshop on Leprosy Research. Treatment of Reactions and Nerve Damage *Int. J. Lepr. Other Mycobact. Dis.,* vol. 64, No. 4, Suppl. S21–S28 (1996).

Neubert, "Teratogenicity: Any Relationship to Carcinogenicity?", *Institute for Toxicology and Embryopharmacology, Free University of Berlin,* Berlin, Federal Rep. Of Germany, pp. 169–178, 1980.

Nguyen, M. et al., "Elevated Levels of the Angiogenic Peptide Basic Fibroblast Growth Factor in Urine of Bladder Cancer Patients", *J. of the Natl. Canc. Inst.,* vol. 85, No. 3, pp. 241–242 (1993).

Nguyen, M. et al., "Elevated Levels of the Angiogenic Peptide Basic Fibroblast Growth Factor in Urine of Patients with a Wide Spectrum of Cancers", *J. of the Natl. Canc. Inst.,* vol. 86, No. 5, pp. 356–361 (1994) (Abstract only).

Nicolas, J., et al., "Interferon Alfa Therapy in Severe Unresponsive Subacute Cutaneous Lupus Erythematosus", *New Engl. J. Med.,* vol. 321, No. 22, pp. 1550–1551 (1989).

Nicolau, et al., "Thalidomide: Treatment of Severe Recurrent Aphthous Stomatatis in Patients with AIDS", *DICP,* vol. 24, No. 11, pp. 1054–1056 (1990).

Nielsen, et al., "Thalidomide Enhances Superoxide Anion Release from Human Polymorphonuclear and Leukocytes", *Acta. Pathol. Microbiol. Immunol. Scand.* [C], vol. 94, No. 6, pp. 233–237 (1986).

Obeso, J. et al., "Methods in Laboratory Investigation A Hemangioendothelioma–Derived Cell Line: Its Use as a Model for the Study of Endothelial Cell Biology", *Laboratory Investigation,* vol. 63, No. 2, pp. 259–269 (1990).

Oikawa, T. et al., "Eponemycin, A Novel Antibiotic is a Highly Powerful Angiogenesis Inhibitor", *Biochem. and Biophy. Res. Comm.,* vol. 181, No. 3, pp. 1070–1077 (1991).

Olson, et al., "Thalidomide (N–phthaloylglutamimide) in the Treatment of Advanced Cancer", *Clin. Pharmacol. Therap.,* vol. 6, No. 3, pp. 292–297 (1965).

Orzalesi, M., "Il Danno Iatrogreno in Neonatologica", *Ped. Med. Chir.,* vol. 14, pp. 105–112 (1992).

Ostraat, et al., "Thalidomide Prolongs Graft Survival in Rat Cardiac Transplants", *Transplant Proc.,* vol. 24, No. 6, pp. 2624–2625 (1992).

Otsuka, et al., "A New Potent Angiogenesis Inhibitor, FR–118487", *J. of Microbiol. and Biotechno.,* vol. 1, No. 3, pp. 163–168 (1991).

Paller, et al., "Proceedings of the Concurrent Sessions", *Pediatr. Dermatol,* vol. 9, No. 4, pp. 397–406 (1992).

Passaniti, A. et al., "Methods in Laboratory Investigation A Simple, Quantitative Method for Assessing Angiogenesis and Antiangiogenic Agents Using Reconstituted Basement Membrane, Heparin, and Fibroblast Growth Factor", *Laboratory Investigation,* vol. 67, No. 4, pp. 519–528 (1992).

Patey, O. et al., "Thalidomide et colite ulcereuse dans la maladie de Behcet", *Gastroenterol. Clin. Biol.,* vol. 13, pp. 104–110 (1989).

Pearson, et al., "Treatment of Moderately Severe Erythema Nodosum Leprosum with Thalidomide—A Double–Blind Controlled Trial", *Lepr. Rev.,* vol. 40, No. 2, pp. 111–116 (1969).

Peyron, et al., "The Pharmacological Basis for the Treatment of Photodermatoses", *Biochimie,* vol. 68, No. 6, pp. 889–904, date unknown.

Pfordte, "Über die Beeinflussung des Serumproperdinsystems Dutch Verschiedene Arzneimittel", *Pharmazie,* vol. 26, pp. 301–302 (1971).

Phillips, et al., "Tumor Necrosis Factor Alpha (rhTNF) Fails to Stimulate Angiogenesis in the Rabbit Cornea", *Anatomical Rec.*, vol. 245, pp. 53–56 (1996).

Powell, R.J. et al., "Investigation and Treatment of Orogenital Ulceration: studies on a Possible Mode of Action of Thalidomide", *Br. J. of Dermatol.*, vol. 113, Supp. 28, pp. 141–144 (1985).

Prigent, F. et al., "Sarcoidose cutanee Traitement par la Thalidomide", *La Presse Medicale,* vol. 12, No. 47, p. 3007 (1983).

Proenca, N.G., "Thalidomide: An Eclectic Medication in Dermatology", *Rev. Paul. Med.*, vol. 107, No. 1, pp. 41–46. (Abstract Only), date unknown.

Radeff, et al., "Recurrent Aphthous Ulcer in Patient Infected with Human Immunodeficiency Virus: Successful Treatment with Thalidomide", *J. Am. Acad. Dermatol*, vol. 23, No. 3, Pt. 1, pp. 523–525 (1990).

Rainsford, K.D., "Disease–Modifying Antirheumatic and Immunoregulatory Agents", *Bailliere's Clinical Rheumatology,* vol. 4, No. 3, pp. 405–432 (1990).

Rajan, et al., "A Clinical Study of Thalidomide Comparing Pre–Treatment and Post–Treatment Reactional Episodes and Corticosteroid Requirements", *Lepr. India,* vol. 55, No. 1, 111–116 (1983).

Randall, T., "Investigational New Drug (US) 'Orphan' Trials now Use Thalidomide from two Sources", *JAMA,* vol. 263, No. 11, p. 1474 (1990).

Randall, T., "Thalidomide's Back in the News, but in more Favorable Circumstances", *JAMA,* vol. 263, No. 11, pp. 1467–1468 (1990).

Revuz, J., "Actualite Du Thalidomide", *Ann. Dermatol. Venereol.*, vol. 117, pp. 313–321 (1990).

Revuz, J. et al., "Crossover Study of Thalidomide vs. Placebo in Severe Recurrent Aphthous Stomatitis", *Arch. Dermatol,* vol. 126, pp. 923–927 (1990).

Rhoton, A. J., "Role for Thalidomide in Primary Biliary Cirrhosis Treatment?", *Gastroenterology,* vol. 105, No. 3, p. 956 (1993).

Robbins, K. C., "The Plasminogen–Plasmin Enzyme System", *Fibrinolysis,* pp. 340–357 (??), date unknown.

Roe, F.J.C., "Pathology Thalidomide and Neoplasia", *Nature,* vol. 200, pp. 1016–1017 (1963).

Roe, et al., "Tumour–Incidence in Progeny of Thalidomide––Treated Mice", *British J. Cancer,* pp. 331–333, (1965).

Ruggenini, et al., "Thalidomide e Tumori Sperimentali", *Cancro,* vol. 20, pp. 39–55 (1967).

Rustin, et al., "*Pyoderma Gangrenosum* Associated with Behcet's Disease: Treatment with Thalidomide", *J. Am. Acad. Dermatol,* vol. 23, No. 5, Pt. 1, pp. 941–944 (1990).

Ryan, et al., "Thalidomide to Treat Esophageal Ulcer in AIDS (6)", *New Engl. J. Med.*, vol. 327, No. 3, pp. 208–209 (1992).

Salven, P. et al., "Serum Vascular Endothelial Growth Factor Is Often Elevated in Disseminated Cancer", *Clinical Cancer Research,* vol. 3, pp. 647–651 (1997).

Sampaio, et al., "Prolonged Treatment with Recombinant Interferon Gamma Induces Erythema Nodosum Lepromatous Leprosy Patients", *J. Exp. Med.,* vol. 175, No. 6, pp. 1729–1737 (1992).

Sampaio, et al., "Thalidomide Selectively Inhibits Tumor Necrosis Factor Alpha Production by Stimulated Human Monocytes", *J. Exp. Med.,* vol. 173, No. 3, pp. 699–703 (1991).

Santis, H.R., "Aphthous Stomatitis and its Management", *Curr. Opin. Dent,* vol. 1, No. 6, pp. 763–768 (1991) (Abstract Only).

Santos, et al., "In Vitro Tumor Necrosis Factor Production by Mononuclear Cells from Lepromatous Leprosy Patients and from Patients with Erythema Nodosumleprosum", *Clin. Immunol. Immunopathol.,* vol. 67, No. 3 I, pp. 199–203 (1993).

Sato, K. et al., "Increased Concentration of Vascular Endothelial Growth Factor/Vascular Permeability Factor in Cyst Fluid of Enlarging and Recurrent Thyroid Nodules", *Journal of Clinical Endocrinology and Metabolism,* vol. 82, No. 6, pp. 1968–1972 (1997).

Schweigerer, L. et al., "Angiogenesis and Angiogenesis Inhibitors in Paediatric Diseases", *European J. of Pediatric,* vol. 151, pp. 472–476 (1992).

Shannon, et al., "Inhibition of de Novo IgM Antibody Synthesis by Thalidomide as a Relevant Mechanism of Action in Leprosy", *Scand. J. Immunol.,* vol. 13, No. 6, pp. 553–562 (1981).

Shannon, et al., "Thalidomide's Effectiveness in Erythema Nodosum Leprosum is Associated with a Decrease in CD4+ Cells in the Peripheral Blood", *Lepr. Rev.,* vol. 63, No. 1, pp. 5–11 (1992).

Shealy, Y.F. et al., "D–and–L–Thalidomide", *Chemistry and Industry,* pp. 1030–1031 (1965).

Sheehan, N.J., "Thalidomide Neurotoxity and Rheumatoid Arthritis", *Arthritis and Rheuma.,* vol. 19, No. 10, p. 1296 (1986).

Sherman, M. et al., "Thalidomide: A Twenty–Five Year Perspective", *Food Drug Cosmetic Law J.,* vol. 41, pp. 458–466 (1986).

Sheskin, J., "The Treatment of Lepra Reaction in Lepromatous Leprosy. Fifteen Years' Experience with Thalidomide", *Int. J. Dermatol.,* vol. 19, No. 6, pp. 318–322 (1980).

Sheskin, et al., "In Vivo Measurements of Iron, Copper and Zinc in the Skin of Prurigo Nodularis Patients Treated with Thalidomide", *Dermatologica,* vol. 162, No. 2, pp. 86–90 (1981).

Shi, G. et al., "Kringle Domains and Plasmin Denaturation", *Biochem. and Biophys. Res. Comm.,* vol. 178, No. 1, pp. 360–368 (1991).

Schumacher, H. et al. "The Metabolism of Thalidomide: The Fate of Thalidomide and Some of its Hydrolysis Products in Various Species", *Brit. J. Pharmacol.,* vol. 25, pp. 338–351 (1965).

Sidky, Y. et al., "Inhibition of Angiogenesis by Interferons: Effects on Tumor–and Lymphocyte–induced Vascular Responses", *Canc. Res.,* vol. 47, pp. 5155–5161 (1987).

Silverman, W.A., "Medical Inflation", *Persp. Biol. Med.,* pp. 617–637 (1980).

Smith, et al., "Studies on the Relationship Between the Chemical Structure and Embryotoxic Activity of Thalidomide and Related Compounds", *Chemical Structure and Embryopathy,* pp. 194–209, date unknown.

Srivastava, A. et al.,"The Prognostic Significance of Tumor Vascularity in Intermediate–Thickness Skin Melanoma", *Am. J. Pathol.,* vol. 133, pp. 419–423 (1988) (abstract from Medline: Accession No. 06745734).

Style, A., "Early Diagnosis and Treatment of Leprosy in the United States", *American Family Physician,* vol. 52, No. 1, 172–178 (1995).

Sugiura, et al., "Effect of Thalidomide on Transplantable Mouse, Rat, and Hamster Tumors", *GANN,* vol. 55, pp. 57–60 (1964).

Suzuki, H, "The History of Iatrogenic Diseases in Japan", *First Department of Internal Medicine, University of Envir. And Occup. Health,* Kitakyushu, Japan, pp. 35–40, date unknown.

Swift, T.R., "Thalidomide in Erythema Nodusum Leprosum", *Lancet,* vol. 2, No. 835, p. 966 (1973).

Szydlowska, et al., "On the Application of Thalidomide as a Block of Functional Groups of Proteins in Histochemical Investigations", *Folia Histo. Cytochem.,* vol. 16, No. 3, pp. 233–240 (1978).

Tamura, et al., "Combination Thalidomide and Cyclosporine for Cardiac Allograft Rejection. Comparison with Combination Methylprodnisolone and Cyclosporine", *Transplantation,* vol. 49, No. 1, p. 20–25 (1990).

Tanaka, Y. et al., "Vascular Endothelial Growth Factor in Diabetic Retinopathy", *The Lancet,* vol. 349, p.1520 (1997).

Taylor, S. et al., "Protamine is an Inhibitor of Angiogenesis", *Nature,* vol. 297, pp. 307–312 (1982).

Teppo, L. et al., "Thalidomide–Type Malformations and Subsequent Osteosarcoma", *The Lancet,* vol. II, No. 8034, p. 405 (1977).

"Thalidomide 20 Years On", *The Lancet,* vol. II, No. 8245, pp. 510–511 (1981).

"Thalidomide", *The Merck Index,* 11th ed., p. 1458 (1989).

Theophilus, S., "Treatment with Thalidomide in Steroid Dependency and Neuritis", *Lepr. India,* vol. 52, No. 3, pp. 423–428 (1980).

Thomas, et al., "Effect of Thalidomide on Liver Regeneration in Rat", *Indian J. Exp. Biol.,* vol. 10, pp. 314–315 (1972).

Thomas, et al., "Lack of Thalidomide Induced Aplasia in Regenerating Tail of Lizard, *Hemidactylus Flavivirdis", Indian J. Exp. Biol.,* vol. 10, pp. 316–317 (1972).

Thomas, L. et al., "Successful Treatment of Adult's Langerhans Cell Histocytosis with Thalidomide", *Archives of Dermatol.,* vol. 129, pp. 1261–1264 (1993).

Torry, R. J. et al., "Angiogenesis in the Uterus: Potential Regulation to Tumor Angiogenesis", *Am. J. of Reproductive Immunology,* vol. 27, pp. 171–179 (1992).

Traldi, et al., "L'impiego Dell'imide Dell'Acido N'ftalilglutammico (Talidomide) Nella Terapia Sintomatica del Vomito di Molti Pazienti Affeti da Neoplasie Maligne o Causato Dalla Somministrazione di Cloridato di Mecloretamina", *Cancro,* vol. 18, pp. 336–341 (1965).

Trautman, J. R., "Treatment of Hansen's Disease", *Cutis,* vol. 18k, No. 1, 62–65 (1976).

Van den Broek, H., "Treatment of Prurigo Nodularis with Thalidomide", *Arch. Dermatol,* vol. 116, No. 5, pp. 571–572 (1980).

Vasilescu, et al., "Cercetari Privind Actiunea Talidomidei Asupra Celulelor Cultivate in Vitro", *Cerc. Fiziol.,* vol. 13, No. 4, pp. 293–300 (1968).

Verhaul, et al., "Combination Oral Antiangiogenic Therapy with Thalidomide and Sulindac Inhibits Tumor Growth in Rabbits", *Brit. J. Cancer,* vol. 79, No. 1, pp. 114–118 (1999).

Vicente, T. et al., "In Vitro Activity of Thalidomide Against *Mycobacterium avium* Complex", *Archives of Internal Medicine,* vol. 153, p.334 (1993).

Villa, et al. ,"Antimyotic Effect of Thalidomide and its Metabolites on the Chick Embryo Bloods Cells", *Haematol. Latina,* vol. 6, pp 217–221 (1963).

Villa, et al., "Cytological Effects of Thalidomide", *The Lancet,* pp. 725 (1963).

Vladutiu, A., "Another Chance for Thalidomide?", *The Lancet,* vol. I, No. 7444, pp. 981–982 (1966).

Vogelsang, G. B. et al., "Thalidomide for the Treatment of Chronic Graft–Versus–Host Disease", *New England J. of Med.,* vol. 326, pp. 1055–1059 (1992).

Vogelsang, et al., "Therapy of Chronic Graft–v–Host Disease in a Rat Model", *Blood,* vol. 74, No. 1, pp. 507–511 (1989).

Vogelsang, et al., "Thalidomide Induction of Bone Marrow Transplantation Tolerance", *Transplant Proc.,* vol. 19, No. 1, Pt. 3, pp. 2658–2661 (1987).

Vogelsang, et al., "Treatment and Prevention of Acute Graft–versus–Host Disease with Thalidomide in a Rat Model", *Transplantation,* vol. 41, No. 5, pp. 644–647 (1986).

Vogt, B. et al., "Inhibition of Angiogenesis in Kaposi's Sarcoma by Captopril", *The Lancet,* vol. 349, p. 1148 (1997).

Waters, M.F. et al., "Treatment of Ulcerative Colitis with Thalidomide", *Brit. Med. J.,* vol. 1, No. 6166, pp. 792 (1979).

Waters, M., "Use of Thalidomide in Leprosy", *BMJ,* vol. 303, No. 6800, p. 470 (1991).

Waters, M.F., "An Internally–Controlled Double Blind Trial of Thalidomide in Severe Erythema Nodosum Leprosum", *Lepro. Rev.,* vol. 42, No. 1, pp. 26–42 (1971).

Weidner, J. et al., "Tumor Angiogenesis and Metastasis-–Correlation in Invasive Breast Carcinoma", *The New England J. of Med.,* vol. 324, No. 1, pp. 1–8 (1991).

Weidner, N. et al., "Tumor Angiogenesis Correlates with Metastasis in Invasive Prostate Cancer", *Am. J. of Pathol.,* vol. 143, No. 2, pp. 401–409 (1993).

Weidner, N. et al., "Tumor Angiogenesis: A New Significant and Independent Prognostic Indicator in Early–Stage Breast Carcinoma", *J. of Nat. Canc. Inst.,* vol. 84, No. 24, 1875–1887 (1992).

Wesolowski, et al., "Effect of Light on a Murine Model of Retinopathy of Prematurity", *Invest. Ophthalmol. & Visual Science,* vol. 33, No. 4, p. 1281 (Abstract only), 1994.

White, C. W. et al., "Treatment of Pulmonary Hemangiomatosis with Recombinant Interferon Alfa–2a", *The New England J. of Med.,* vol. 32, No. 18, pp. 1197–1200 (1989).

Williams, K. M., "Enantiomers in Arthritic Disorders", *Pharmacol. & Therapeutics,* vol. 46, No. 2, pp. 273–295 (1990).

Williams, et al., "Thalidomide Hypersensitivity in AIDS", *Lancet,* vol. 337, pp. 436–437 (1991).

Winkelmann, et al., "Thalidomide Treatment of Prurigo Nodularis", *Acta Derm. Venereol.,* vol. 64, No. 5, pp. 412–417 (1984).

Wood, et al., "The Potential use of Thalidomide in the Therapy of Graft–versus–Host Disease—A Review of Clinical and Laboratory Information", *Leuk. Res. ,* vol. 14, No. 5, pp. 395–399 (1990).

Woodyatt, P.B., "Thalidomide", *The Lancet,* p. 750. (1962).

Wulff, et al., "Development of Polyneuropathy During Thalidomide Therapy", *Br. J. Dermatol.,* vol. 112, No. 4, pp. 475–480 (1985).

Yazici, et al., "Practical Treatment Recommendations for Pharmacology of Behcet's Syndrome", *Drugs,* vol. 42, No. 5, pp. 796–804 (1991).

Yoshimura, T. et al., "Cloning, Sequencing, and Expression of Human Macrophage Stimulating Protein (MSP, MST1) Confirms MSP as a Member of the Family of Kringle Proteins and Locates the MSP Gene on Chromosome 3", *The J. of Biol. Chem.,* vol. 268, No. 21, pp. 15461–15468 (1993).

Youle, et al., "Treatment of Resistant Aphthous Ulceration with Thalidomide in Patients Positive for HIV Antibody", *BMJ,* vol. 298, No. 6671, p. 432 (1989).

Youle, et al., "Thalidomide in Hyperalgic Pharyngeal Ulceration of AIDS", *Lancet,* vol. 335, No. 8705, p. 1591 (1990).

Yue, t. et al., "2–Methoxyestradiol, an Endogenous Estrogen Metabolite, Induces Apoptosis in Endothelial Cells and Inhibits Angiogenesis: Possible Role for Stress–Activated Protein Kinase Signaling Pathway and Fas Expression", *Molecular Pharmacology,* vol. 51, pp. 951–962 (1997).

Ziche, M. et al., "Nitric Oxide Synthase Lies Downstream from Vascular Endothelial Growth Factor–induced but Not Basic Fibroblast Growth Factor–Induced Angiogenesis", *J. Clin. Invest.,* vol. 99, No. 11, pp. 2625–2634 (1997).

Zwart, D., "Treatment of Grade II Astrocytoma with Thalidomide", *Arzneim.–Forsch.,* vol. 16, No. 12, pp. 1688–1689 (1966).

* cited by examiner

AMINO DERIVATIVES OF EM-138 AND METHODS OF TREATING ANGIOGENESIS WITH SAME

CROSS-REFERENCE TO RELATED APPLICATIONS

This application is a continuation of U.S. application Ser. No. 09/545,139, filed Apr. 7, 2000, which is a division of U.S. application Ser. No. 08/950,673, filed Oct. 16, 1997, now U.S. Pat. No. 6,071,948, which is a continuation of U.S. application Ser. No. 08/468,792, filed Jun. 6, 1995, now U.S. Pat. No. 5,712,291, which is a continuation of U.S. application Ser. No. 08/168,817, filed Dec. 15, 1993, now U.S. Pat. No. 5,629,327, which is a continuation-in-part of U.S. application Ser. No. 08/025,046, filed Mar. 1, 1993, now abandoned.

TECHNICAL FIELD

The present invention relates to methods and compositions for preventing unwanted angiogenesis in a human or animal. More particularly, the present invention relates to a method for preventing unwanted angiogenesis, particularly in angiogenesis dependent or associated diseases, by administration of compounds such as thalidomide and related compounds.

BACKGROUND OF THE INVENTION

As used herein, the term "angiogenesis" means the generation of new blood vessels into a tissue or organ. Under normal physiological conditions, humans or animals only undergo angiogenesis in very specific restricted situations. For example, angiogenesis is normally observed in wound healing, fetal and embryonal development and formation of the corpus luteum, endometrium and placenta. The control of angiogenesis is a highly regulated system of angiogenic stimulators and inhibitors. The control of angiogenesis has been found to be altered in certain disease states and, in many cases, the pathological damage associated with the disease is related to the uncontrolled angiogenesis.

Both controlled and uncontrolled angiogenesis are thought to proceed in a similar manner. Endothelial cells and pericytes, surrounded by a basement membrane, form capillary blood vessels. Angiogenesis begins with the erosion of the basement membrane by enzymes released by endothelial cells and leukocytes. The endothelial cells, which line the lumen of blood vessels, then protrude through the basement membrane. Angiogenic stimulants induce the endothelial cells to migrate through the eroded basement membrane. The migrating cells form a "sprout" off the parent blood vessel, where the endothelial cells undergo mitosis and proliferate. The endothelial sprouts merge with each other to form capillary loops, creating the new blood vessel. In the disease state, prevention of angiogenesis could avert the damage caused by the invasion of the new microvascular system.

Persistent, unregulated angiogenesis occurs in a multiplicity of disease states, tumor metastasis and abnormal growth by endothelial cells and supports the pathological damage seen in these conditions. The diverse pathological states created due to unregulated angiogenesis have been grouped together as angiogenic dependent or angiogenic associated diseases. Therapies directed at control of the angiogenic processes could lead to the abrogation or mitigation of these diseases.

One example of a disease mediated by angiogenesis is ocular neovascular disease. This disease is characterized by invasion of new blood vessels into the structures of the eye such as the retina or cornea. It is the most common cause of blindness and is involved in approximately twenty eye diseases. In age-related macular degeneration, the associated visual problems are caused by an ingrowth of chorioidal capillaries through defects in Bruch's membrane with proliferation of fibrovascular tissue beneath the retinal pigment epithelium. Angiogenic damage is also associated with diabetic retinopathy, retinopathy of prematurity, corneal graft rejection, neovascular glaucoma and retrolental fibroplasia. Other diseases associated with corneal neovascularization include, but are not limited to, epidemic keratoconjunctivitis, Vitamin A deficiency, contact lens overwear, atopic keratitis, superior limbic keratitis, pterygium keratitis sicca, sjogrens, acne rosacea, phylectenulosis, syphilis, Mycobacteria infections, lipid degeneration, chemical burns, bacterial ulcers, fungal ulcers, *Herpes simplex* infections, *Herpes zoster* infections, protozoan infections, Kaposi sarcoma, Mooren ulcer, Terrien's marginal degeneration, mariginal keratolysis, rheumatoid arthritis, systemic lupus, polyarteritis, trauma, Wegeners sarcoidosis, Scleritis, Steven's Johnson disease, pemphigoid, radial keratotomy, and corneal graph rejection.

Diseases associated with retinal/choroidal neovascularization include, but are not limited to, diabetic retinopathy, macular degeneration, sickle cell anemia, sarcoid, syphilis, pseudoxanthoma elasticum, Pagets disease, vein occlusion, artery occlusion, carotid obstructive disease, chronic uveitis/vitritis, mycobacterial infections, Lyme's disease, systemic lupus erythematosis, retinopathy of prematurity, Eales disease, Bechets disease, infections causing a retinitis or choroiditis, presumed ocular histoplasmosis, Bests disease, myopia, optic pits, Stargarts disease, pars planitis, chronic retinal detachment, hyperviscosity syndromes, toxoplasmosis, trauma and post-laser complications. Other diseases include, but are not limited to, diseases associated with rubeosis (neovasculariation of the angle) and diseases caused by the abnormal proliferation of fibrovascular or fibrous tissue including all forms of proliferative vitreoretinopathy.

Another disease in which angiogenesis is believed to be involved is rheumatoid arthritis. The blood vessels in the synovial lining of the joints undergo angiogenesis. In addition to forming new vascular networks, the endothelial cells release factors and reactive oxygen species that lead to pannus growth and cartilage destruction. The factors involved in angiogenesis may actively contribute to, and help maintain, the chronically inflamed state of rheumatoid arthritis.

Factors associated with angiogenesis may also have a role in osteoarthritis. The activation of the chondrocytes by angiogenic-related factors contributes to the destruction of the joint. At a later stage, the angiogenic factors would promote new bone formation. Therapeutic intervention that prevents the bone destruction could halt the progress of the disease and provide relief for persons suffering with arthritis.

Chronic inflammation may also involve pathological angiogenesis. Such disease states as ulcerative colitis and Crohn's disease show histological changes with the ingrowth of new blood vessels into the inflamed tissues. Bartonellosis, a bacterial infection found in South America, can result in a chronic stage that is characterized by proliferation of vascular endothelial cells. Another pathological role associated with angiogenesis is found in atherosclerosis. The plaques formed within the lumen of blood vessels have been shown to have angiogenic stimulatory activity.

One of the most frequent angiogenic diseases of childhood is the hemangioma. In most cases, the tumors are benign and regress without intervention. In more severe cases, the tumors progress to large cavernous and infiltrative forms and create clinical complications. Systemic forms of hemangiomas, the hemangiomatoses, have a high mortality rate. Therapy-resistant hemangiomas exist that cannot be treated with therapeutics currently in use.

Angiogenesis is also responsible for damage found in hereditary diseases such as Osler-Weber-Rendu disease, or hereditary hemorrhagic telangiectasia. This is an inherited disease characterized by multiple small angiomas, tumors of blood or lymph vessels. The angiomas are found in the skin and mucous membranes, often accompanied by epistaxis (nosebleeds) or gastrointestinal bleeding and sometimes with pulmonary or hepatic arteriovenous fistula.

Angiogenesis is prominent in solid tumor formation and metastasis. Angiogenic factors have been found associated with several solid tumors such as rhabdomyosarcomas, retinoblastoma, Ewing sarcoma, neuroblastoma, and osteosarcoma. A tumor cannot expand without a blood supply to provide nutrients and remove cellular wastes. Tumors in which angiogenesis is important include solid tumors, and benign tumors such as acoustic neuroma, neurofibroma, trachoma and pyogenic granulomas. Prevention of angiogenesis could halt the growth of these tumors and the resultant damage to the animal due to the presence of the tumor.

It should be noted that angiogenesis has been associated with blood-born tumors such as leukemias, any of various acute or chronic neoplastic diseases of the bone marrow in which unrestrained proliferation of white blood cells occurs, usually accompanied by anemia, impaired blood clotting, and enlargement of the lymph nodes, liver, and spleen. It is believed that angiogenesis plays a role in the abnormalities in the bone marrow that give rise to leukemia-like tumors.

Angiogenesis is important in two stages of tumor metastasis. The first. stage where angiogenesis stimulation is important is in the vascularization of the tumor which allows tumor cells to enter the blood stream and to circulate throughout the body. After the tumor cells have left the primary site, and have settled into the secondary, metastasis site, angiogenesis must occur before the new tumor can grow and expand. Therefore, prevention of angiogenesis could lead to the prevention of metastasis of tumors and possibly contain the neoplastic growth at the primary site.

Knowledge of the role of angiogenesis in the. maintenance and metastasis of tumors has led to a prognostic indicator for breast cancer. The amount of neovascularization found in the primary tumor was determined by counting the microvessel density in the area of the most intense neovascularization in invasive breast carcinoma. A high level of microvessel density was found to correlate with tumor recurrence. Control of angiogenesis by therapeutic means could possibly lead to cessation of the recurrence of the tumors.

Angiogenesis is also involved in normal physiological processes such as reproduction and wound healing. Angiogenesis is an important step in ovulation and also in implantation of the blastula after fertilization. Prevention of angiogenesis could be used to induce amenorrhea, to block ovulation or to prevent implantation by the blastula.

In wound healing, excessive repair or fibroplasia can be a detrimental side effect of surgical procedures and may be caused or exacerbated by angiogenesis. Adhesions are a frequent complication of surgery and lead to problems such as small bowel obstruction.

Several kinds of compounds have been used to prevent angiogenesis. Taylor et al. have used protamine to inhibit angiogenesis, see Taylor et al., Nature 297:307 (1982). The toxicity of protamine limits its practical use as a therapeutic. Folkman et al. have disclosed the use of heparin and steroids to control angiogenesis. See Folkinan et al., Science 221:719 (1983) and U.S. Pat. Nos. 5,001,116 and 4,994,443. Steroids, such as tetrahydrocortisol, which lack gluco and mineral corticoid activity, have been found to be angiogenic inhibitors.

Other factors found endogenously in animals, such as a 4 kDa glycoprotein from bovine vitreous humor and a cartilage derived factor, have been used to inhibit angiogenesis. Cellular factors such as interferon inhibit angiogenesis. For example, interferon a or human interferon β has been shown to inhibit tumor-induced angiogenesis in mouse dermis stimulated by human neoplastic cells. Interferon β is also a potent inhibitor of angiogenesis induced by allogeneic spleen cells. See Sidky et al., *Cancer Research* 47:5155–5161 (1987). Human recombinant a interferon (alpha/A) was reported to be successfully used in the treatment of pulmonary hemangiomatosis, an angiogenesis-induced disease. See White et al., *New England J. Med.* 320:1197–1200 (1989).

Other agents which have been used to inhibit angiogenesis include ascorbic acid ethers and related compounds. See Japanese Kokai Tokkyo Koho No. 58-131978. Sulfated polysaccharide DS 4152 also shows angiogenic inhibition. See Japanese Kokai Tokkyo Koho No. 63-119500. A fungal product, fumagillin, is a potent angiostatic agent in vitro. The compound is toxic in vivo, but a synthetic derivative, AGM 12470, has been used in vivo to treat collagen II arthritis. Fumagillin and O-substituted fumagillin derivatives are disclosed in EPO Publication Nos. 0325199A2 and 0357061A1.

PCT Application No. WO 92/14455 to Kaplan et al. is directed to a method for controlling abnormal concentration of TNF-a by administering thalidomide or thalidomide derivatives to a patient with toxic concentrations of TNF-a.

The above compounds are either topical or injectable therapeutics. Therefore, there are drawbacks to their use as a general angiogenic inhibitor and lack adequate potency. For example, in prevention of excessive wound healing, surgery on internal body organs involves incisions in various structures contained within the body cavities. These wounds are not accessible to local applications of angiogenic inhibitors. Local delivery systems also involve frequent dressings which are impracticable for internal wounds, and increase the risk of infection or damage to delicate granulation tissue for surface wounds.

Thus, a method and composition are needed that are capable of inhibiting angiogenesis and which are easily administered. A simple and efficacious method of treatment would be through the oral route. If an angiogenic inhibitor could be given by an oral route, the many kinds of diseases discussed above, and other angiogenic dependent pathologies, could be treated easily. The optimal dosage could be distributed in a form that the patient could self-administer.

SUMMARY OF THE INVENTION

In accordance with the present invention, compositions and methods are provided that are effective in inhibiting unwanted angiogenesis. These compositions are easily administered by different routes including oral and can be given in dosages that are safe and provide angiogenic inhibition at internal sites. The present invention provides a method of treating mammalian diseases mediated by undesired and uncontrolled angiogenesis by administering a composition comprising an anti-angiogenic compound in a dosage sufficient to inhibit angiogenesis.

The present invention also includes angiogenic inhibiting compounds that contain an epoxide group. These angiogenic inhibiting compounds can be administered to a human or animal alone or with epoxide hydrolase inhibiting compounds.

The present invention is especially useful for treating certain ocular neovascular diseases such as macular degeneration. The compounds which are contemplated as part of the present invention preferably can be given orally to the patient and thereby halt the progression of the disease. Other disease that can be treated using the present invention are diabetic retinopathy, neovascular glaucoma and retrolental fibroplasia.

Accordingly, it is an object of the present invention to provide a compound and method to inhibit unwanted angiogenesis in a human or animal.

It is yet another object of the present invention to provide a composition of inhibiting angiogenesis by oral administration of the composition.

It is another object of the present invention to provide a treatment for diseases mediated by angiogenesis.

It is yet another object of the present invention to provide a treatment for macular degeneration.

It is yet another object of the present invention to provide a treatment for all forms of proliferative vitreoretinopathy including those forms not associated with diabetes.

It is yet another object of the present invention to provide a treatment for solid tumors.

It is yet another object of the present invention to provide a method and composition for the treatment of blood-born tumors such as leukemia.

It is another object of the present invention to provide a method and composition for the treatment of hemangioma.

It is another object of the present invention to provide a method and composition for the treatment of retrolental fibroplasia.

It is another object of the present invention to provide a method and composition for the treatment of psoriasis.

It is another object of the present invention to provide a method and composition for the treatment of Kaposi's sarcoma.

It is another object of the present invention to provide a method and composition for the treatment of Crohn's diseases.

It is another object of the present invention to provide a method and composition for the treatment of diabetic retinopathy.

Other features and advantages of the invention will be apparent from the following description of preferred embodiments thereof.

These and other objects, features and advantages of the present invention will become apparent after a review of the following detailed description of the disclosed embodiments and the appended claims.

A)
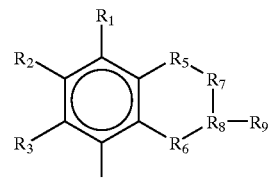

B)
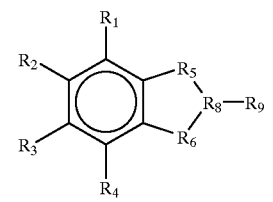

C)
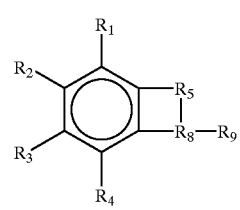

Figure 4:
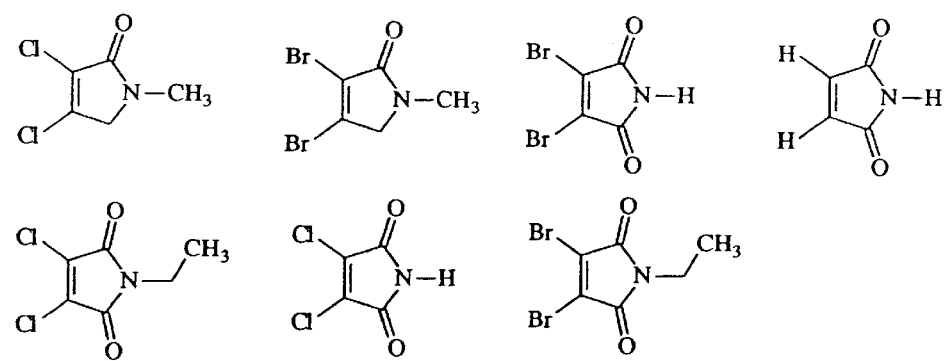

FIG. 4 is a listing of representative compounds in the genus represented by the following general formula:

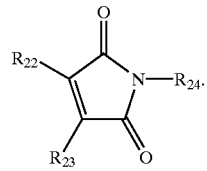

Figure 5:
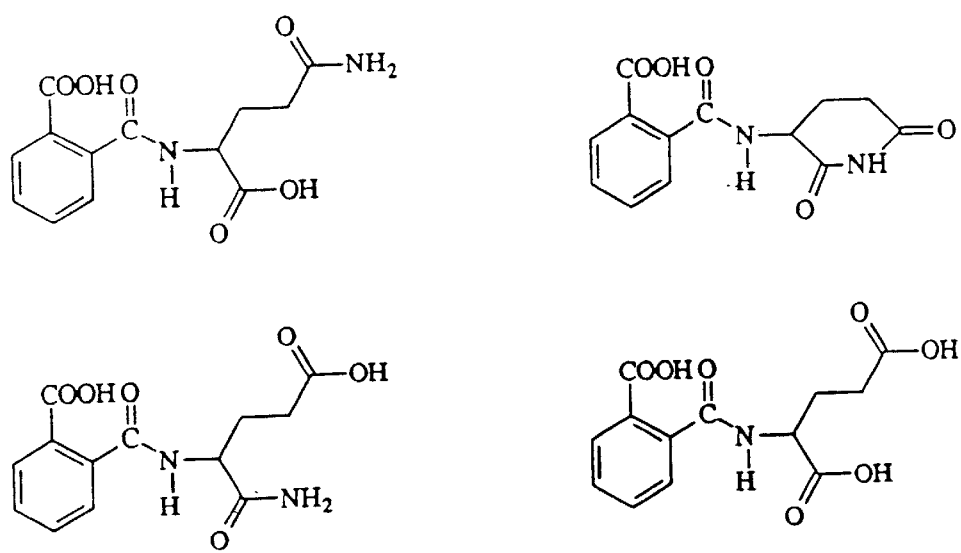

FIG. 5 is a listing of representative compounds in the genus represented by the following general formula:

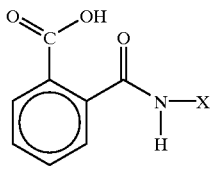

Figure 6:
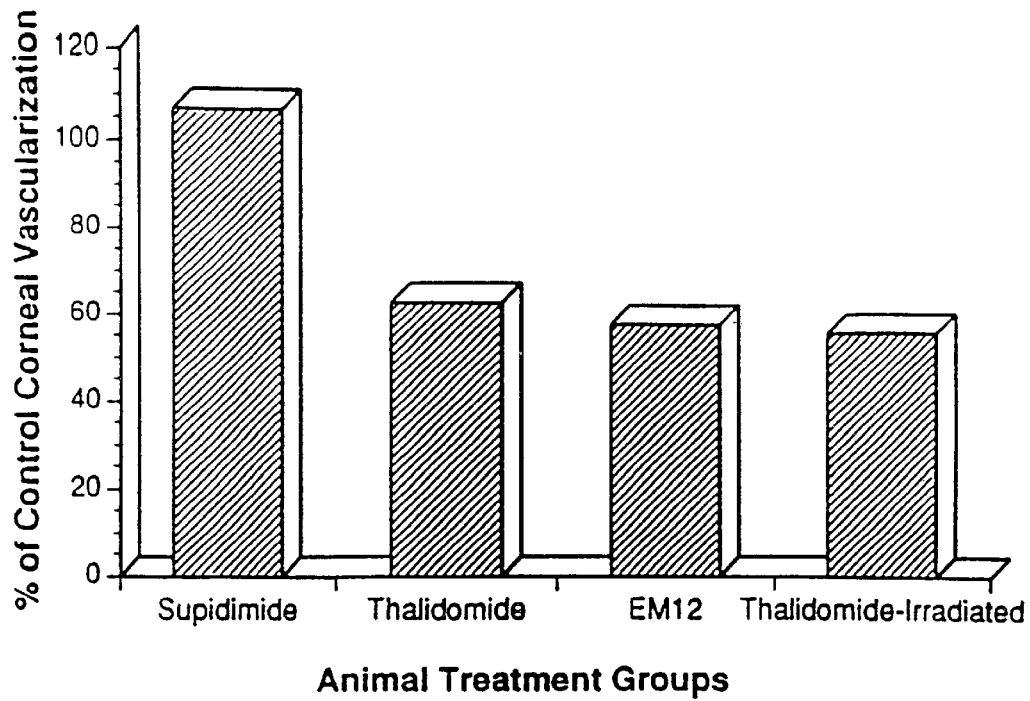

FIG. 6 shows the effect of thalidomide and EM12 on angiogenesis in a rabbit cornea model of angiogenesis.

Figure 7:
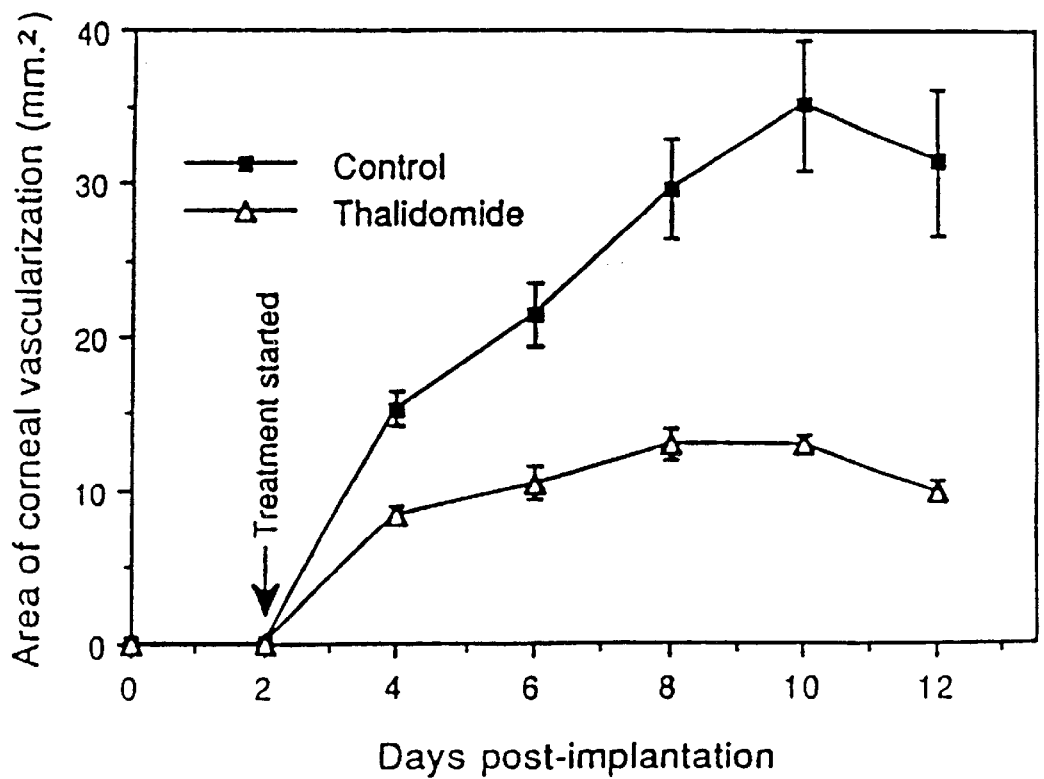

FIG. 7 shows the effect of thalidomide on the area of corneal vascularization in a rabbit cornea model of angiogenesis.

DETAILED DESCRIPTION

The present invention includes compositions and methods for the treatment of diseases that are mediated by angiogenesis. One embodiment of the present invention is the use of thalidomide or the metabolites of thalidomide as disclosed herein to inhibit unwanted angiogenesis. The present invention also includes compounds which cause dysmelia is the developing fetus and have anti-angiogenic. activity. The present invention comprises a method of treating undesired angiogenesis in a human or animal comprising the steps of administering to the human or animal with the undesired angiogenesis a composition comprising an effective amount of a teratogenic compound that is anti-angiogenic.

Compounds that can be used in accordance with the present invention include compounds included in the following general formulae. Examples of compounds that have anti-angiogenic properties having one of the following three formulae (A), (B), or (C):

A)

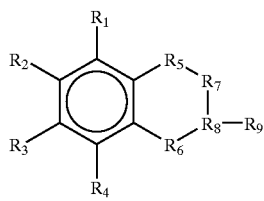

B)

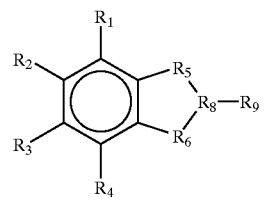

C)

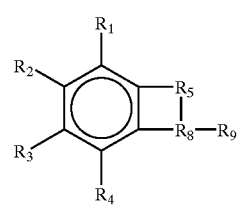

In the above formulae A), B), and C), $R_1$, $R_2$, $R_3$, and R4 can be selected from:—H; —OH; =O, straight chained and branched alkanes, alkenes, alkynes; cyclic alkanes, alkenes, and alkynes; combinations of cyclic and acyclic alkanes, alkenes, and alkynes; alcohol, aldehyde, ketone, carboxylic acid, ester, or ether moieties in comnbination with acyclic, cyclic, or combination acyclic/cyclic moieties; aza; amino; —$XO_n$ or —O—$XO_n$, (where X=N and n=2; X=S and n=2 or 3; or X=P and n=1–3); and halogens.

In the above formulae A), B), and C), $R_5$, $R_6$, and $R_7$ are each independently selected from:

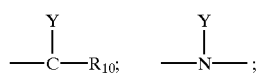

or —O— where Y is optional and is the same as defined above for $R_1$; and where $R_{10}$ is the same as defined above for $R_1$, or (where Y is absent) $R_{10}$ is =O; and where $R_8$ is independently selected from:

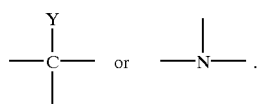

In the above formulae A), B), and C), $R_9$ is a moiety having formula D), E), F), G), or H):

D)

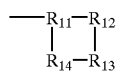

E)

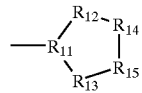

F)

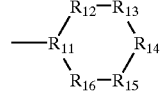

G)

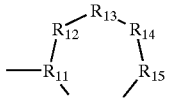

H)

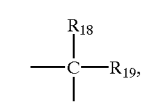

Accordingly, another aspect of the present invention features inhibiting angiogenesis in a mammal by administering a therapeutic composition comprising one of the above-described compounds in a dosage sufficient to inhibit angiogenesis In preferred embodiments, the compound has formula B), where $R_5$ and $R_6$ are selected from the group consisting of: —$CH_2$,

and $R_9$ has formula F) or H); and $R_{14}$ and $R_{16}$ are selected from the group consisting of:

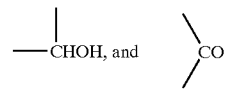

and $R_{15}$ and is —O—, or

Figure 1:
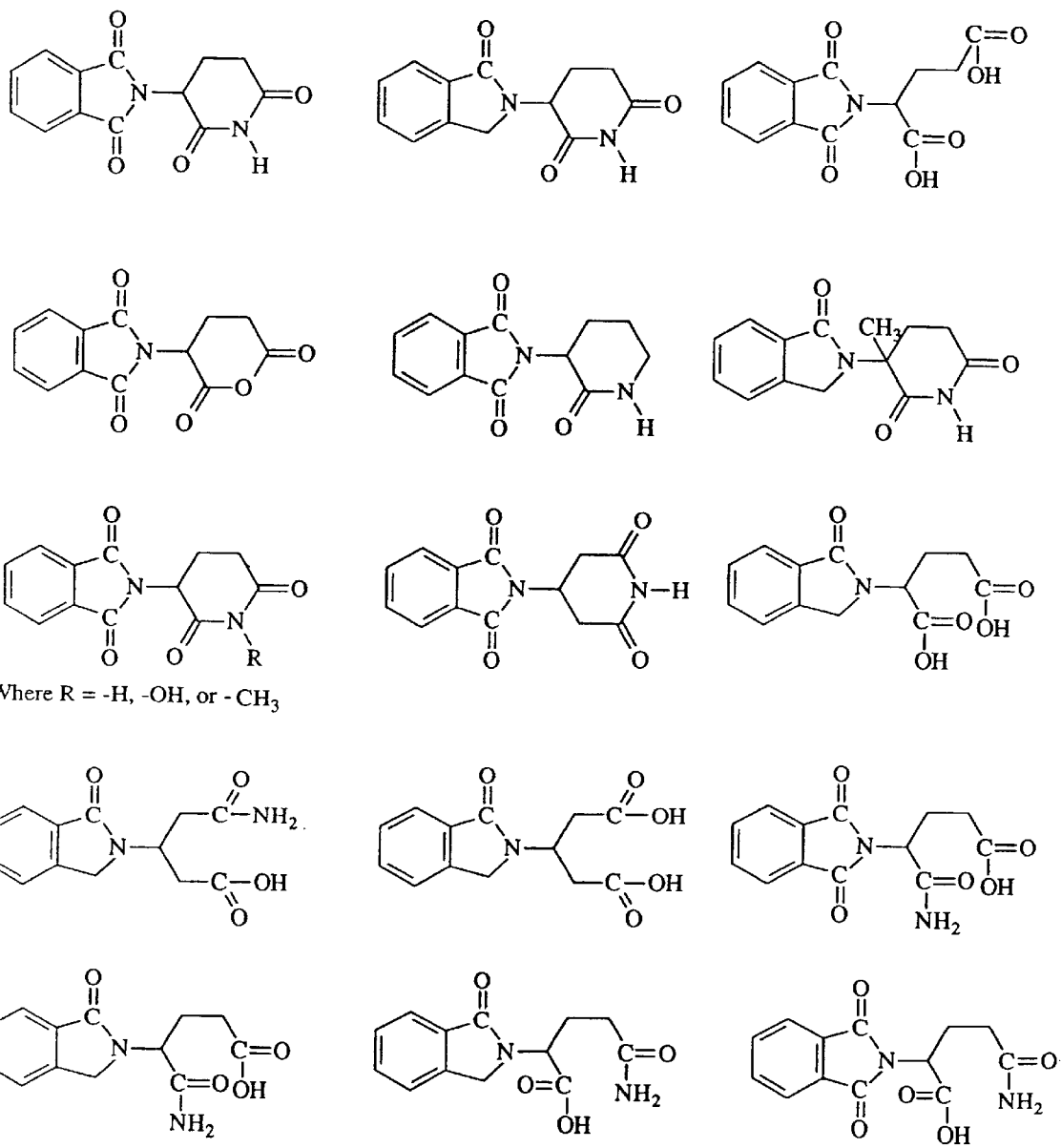
FIGS. 1 through 3 are a listing of representative compounds in the genus represented by the following general formulas.
Figure 2:
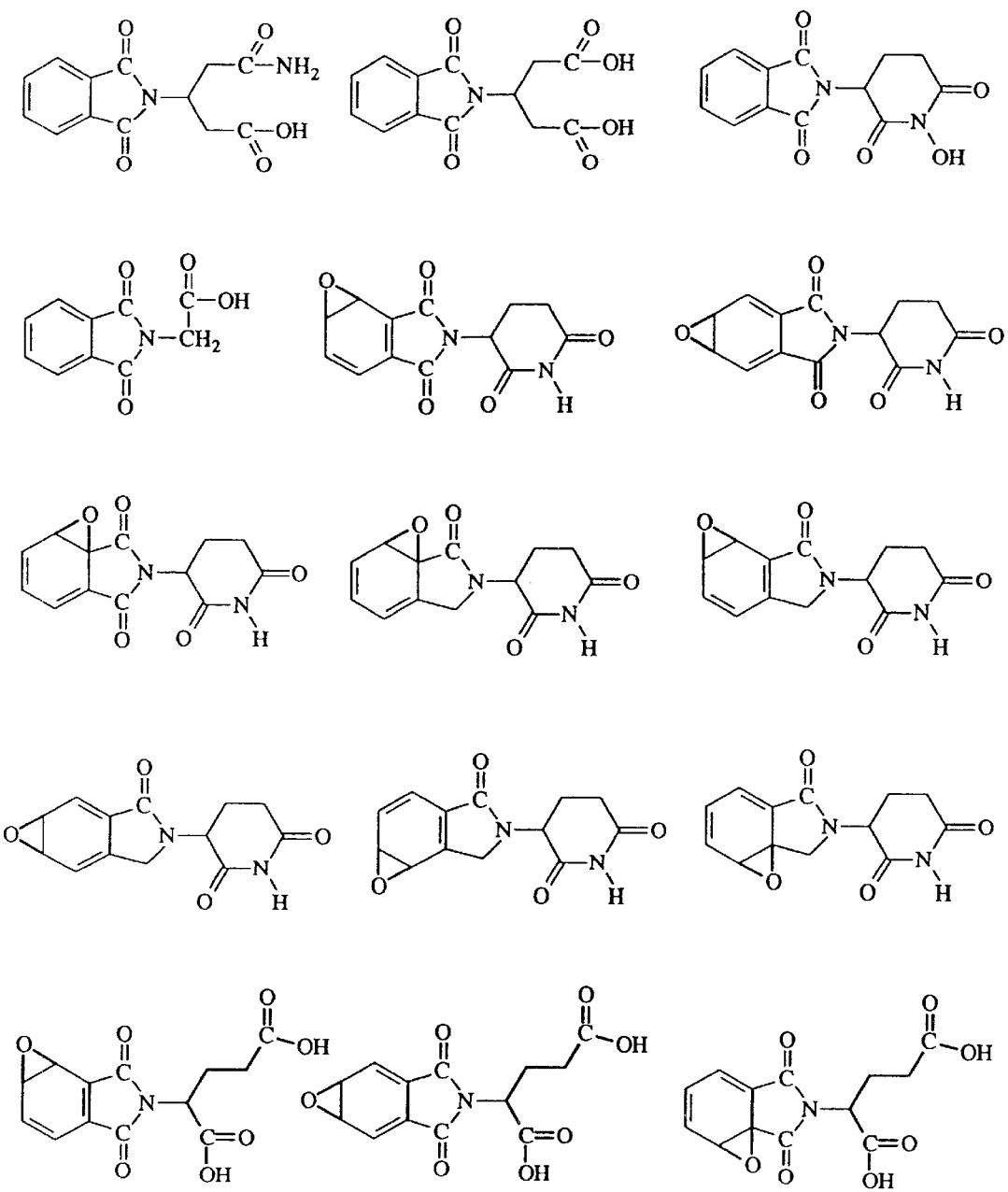
Figure 3:
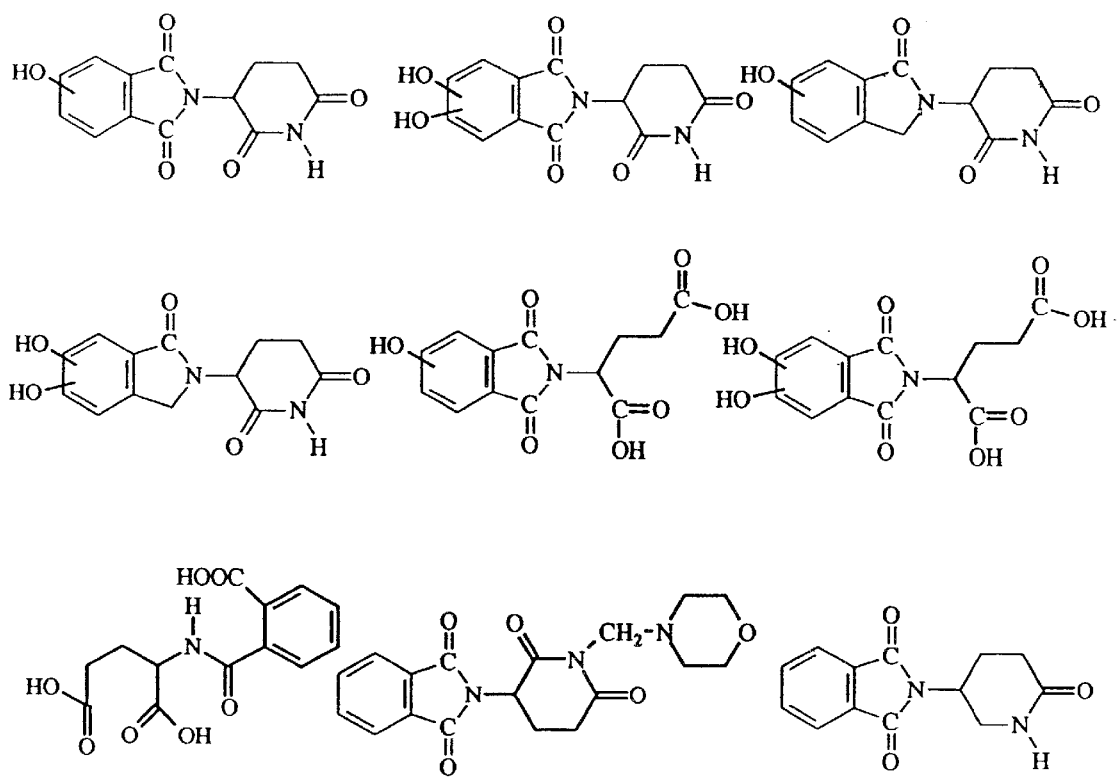

where $R_{21}$ is —H, —$CH_3$, or —OH. Specific preferred compounds according to this aspect of the present invention include thalidomnide, its precursors, metabolites and analogs. Particular analogs include EM-12, N-phthaloyl-DL-glutamic acid (PGA) or N-phthaloyl-DL-glutamine anhydride. Examples of compounds that are members of this genus are listed in FIGS. 1 through 3. It is to be understood that the compounds included as part of the present invention are not to be limited to those compounds shown in FIGS. 1 through 3 and include all other compounds that are members of the genus described by the general formulas herein.

Compounds of the following formula that have anti-angiogenic properties:

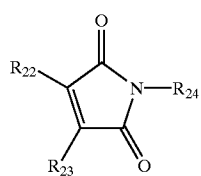

where $R_{22}$ and $R_{23}$ are (independently), —H, —F, —Cl, —Br, —I, —CH$_3$, or —CH$_2$ —CH$_3$; and $R_{24}$ is —H, —CH3, or —CH2 —CH3.

The present invention also features inhibiting angiogenesis in a mammal by administering a compound according to the above formulae in a dosage sufficient to inhibit angiogenesis. Examples of specific compounds that are members of this genus are listed in FIG. 4.

Angiogenesis inhibition hydrolysis products of thalidomide having the following general formula can be used in practicing the present invention:

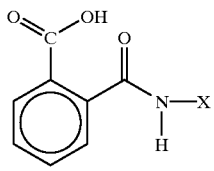

where X is $R_6$ as defined above, or

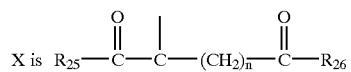

and $R_{25}$ and $R_{26}$ are, independently, —OH, —H, or NH$_2$, and n=1 through 4. Examples of such compounds are shown in FIG. 5.

Angiogenesis inhibition compounds having the following general formula can be used in practicing the present invention:

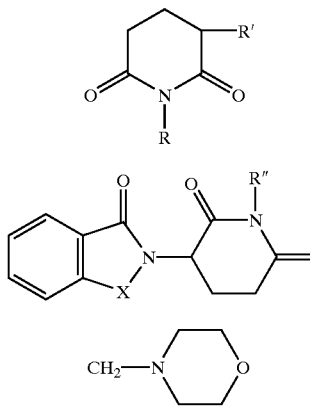

wherein compounds of structure (I), wherein R is selected from the group consisting of hydrogen, alkyl radicals of 1 to 6 carbon atoms, the phenyl radical, and the benzyl radical; and wherein R' is selected from the group consisting of the phthalimido radical and the succinimido radical and of structure (II), wherein X is CH$_2$ or C═O; R" is H, —CH$_2$CH$_3$, —C$_6$H$_5$, —CH$_2$C$_6$H$_5$, —CH$_2$CH═CH$_2$, or (a) and hydrolysis products of the compounds wherein R" is H and the piperidino ring or both the piperidino and the imido ring are hydrolyzed.

Another set of compounds that are considered part of the present invention are the epoxides of thalidomide, EM-12 and EM-138. Representative epoxide compounds are shown as follows:

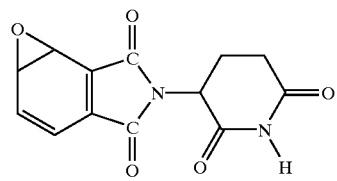

Epoxides of thalidomide

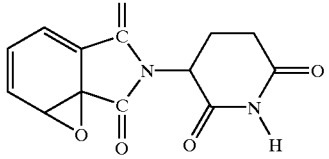

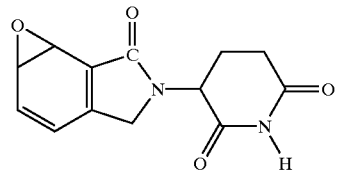

Epoxides of EM 12

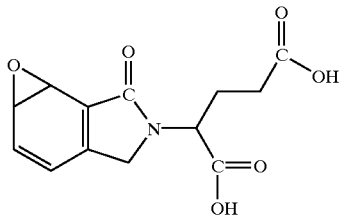

Epoxides of EM 138

It should be understood that the epoxide can be attached at the 6,1 site on the benzene ring, the 1,2 site, the 2,3 site 3,4 or the 4,5 site. All of these compounds are contemplated as part of the present invention.

The epoxides of the thalidomide, EM-12, and EM 138 can be hydrolyzed to the following compounds:

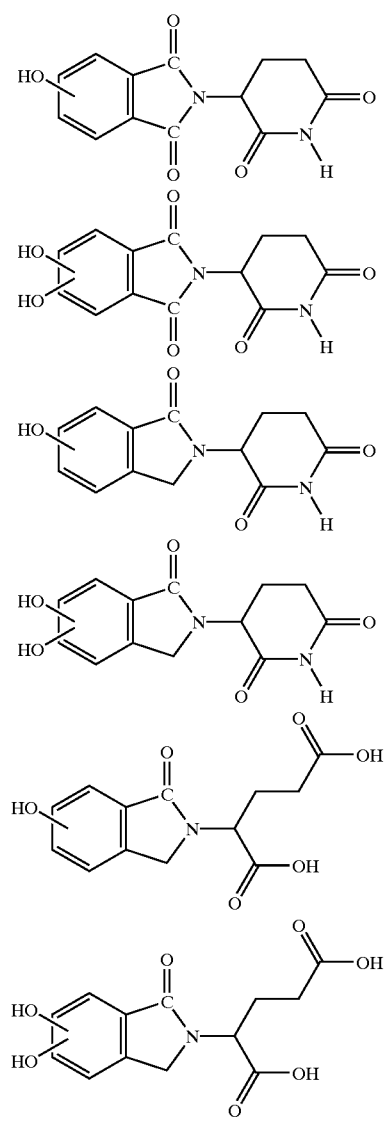

It is to be understood that the hydroxyl group can be on carbons 1, 2, 3, 4, 5 and 6 of the benzene ring. Also contemplated as part of the present invention are dihydroxyl compounds wherein the two hydroxyl groups are located bis to each other on carbons 1, 2, 3, 5 and 6 of the above compounds. The epoxides, the hydrolysis products of the epoxides, and the hydrolysis products of the thalidomide are all contemplated to be part of the present invention.

It is known that epoxides are hydrolized by a group of enzymes known as epoxide hydrolases. There is a class of compounds which are epoxide hydrolase inhibitors. Examples of these compounds are valpromide (2-propylpentanamide) and valproic acid (2-propylpentanoic acid). Because epoxides are important angiogenesis inhibitors, it is contemplated as part of the present invention, compositions comprising any of the angiogenesis inhibitors compounds recited herein in combination with epoxide hydrolase inhibitors. The epoxide hydrolase inhibitors can be administered to a human or animal together or sequentially. The expoxide group appears to be an important substituent common to several angiogenesis inhibitors. The use of epoxide hydrolase inhibitors to potentiate the activity of any angiogenesis inhibitor containing an epoxide is contemplated as part of the present invention. For example, the epoxide hydrolase inhibitors can be administered with the following epoxide-containing anti-angiogenesis compounds: AGM 1470, Eponimycin, microbial metabolites of *Scolecobasidium arenarium* designated f/2015, fr/111142 and fr/18487. See Oikawa, *Biochem Biophys. Res. Comm*, Vol. 81:1070 (1971) and Otsuka, *J. Microbial. Biotech.*, Vol 1:163 (1991).

It is contemplated as an embodiment of the present invention the use of the epoxide containing angiogenesis inhibitors with or without epoxide hydrolase inhibitors as a treatment for diseases mediated by elevated or toxic levels of TNF-a. TNF-a has been recognized as manifesting a dose dependent toxicity. If present at low levels for a long period of time, TNF-a can result in cachexia. Cachexia is a general weight loss and wasting occurring in the course of some chronic diseases such as cancer, opportunistic infections of AIDS, inflammatory diseases, parasitic diseases, tuberculosis, and high dose IL-2 therapy. The epoxide containing angiogenesis inhibitors, with or without epoxide hydrolase inhibitors, are also effective in treating diseases such as septic shock, leprosy and graph vs. host disease.

Other embodiments are within the present invention. For example, other dysmelia-causing compounds can be used according to the present invention, e.g. 4-methylphthalic acid, pyridoxine, vasopressin, acetazolamide, or a compound having the following formula (where R=H, —OH, or —CH$_3$):

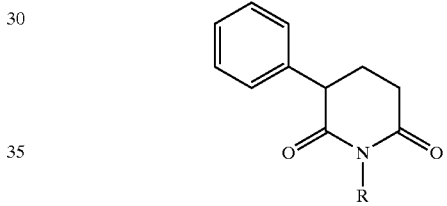

Other compounds which are teratogens, such as valproic acid (2-propylpentanoic acid), the retinoids, such as cis-retinoic acid, and rifampin may also be used in accordance with the invention.

In summary, the preferred compounds are thalidomide, as well as analogs, hydrolysis products, metabolites and precursors of thalidomide that are teratogenic, and, more specifically, that cause dismelia. However, it is to be understood that it is not necessary for a compound to have both teratogenic activity and angiogenesis inhibiting activity to be considered part of the present invention. Dysmelia-causing compounds can be identified by the general procedures of Helm, *Arzneimittleforschung*, 31(i/6):941–949 (1981), in which rabbit pups are examined after exposure to the compound in utero. The compounds can generally be purchased, e.g., from Andrulis Pharmaceuticals, Beltsville, Md., or synthesized according to known procedures. It is to be understood that the compounds of the present invention can exist as enantiomers and that the racemic mixture of enantiomers or the isolated enantiomers are all considered as within the scope of the present invention.

Many of the compounds that are contemplated as part of the present invention can be enriched in optically active enantiomers of the compounds specified above. Specifically, Blaschke has reported that the S enanantiomers may be disproportionately responsible for the dismelia-producing effect of these compounds. See, generally Blaschke, *Arzneimittelforschung* 29:1640–1642 (1979). The above described articles generally describe procedures to obtain optically active preparations of the compounds of interest. See, e.g. Shealy et al., *Chem. Indus.* 1030 (1965); and Casini et al., *Fannaco Ed. Sci.* 19:563 (1964).

The compounds described above can be provided as pharmaceutically acceptable formulations using formulation methods known to those of ordinary skill in the art. These formulations can be administered by standard routes. In general, the combinations may be administered by the topical, transdermal, oral, rectal or parenteral (e.g., intravenous, subcutaneous or intramuscular) route. In addition, the combinations may be incorporated into biodegradable polymers allowing for sustained release of the compound, the polymers being implanted in the vicinity of where drug delivery is desired, for example, at the site of a tumor. The biodegradable polymers and their use are described, for example, in detail in Brem et al., *J. Neurosurg.* 74:441–446 (1991).

The dosage of the compound will depend on the condition being treated, the particular compound, and other clinical factors such as weight and condition of the human or animal and the route of administration of the compound. It is to be understood that the present invention has application for both human and veterinary use. For oral administration to humans, a dosage of between approximately 0.1 to 300 mg/kg/day, preferably between approximately 0.5 and 50 mg/kg/day, and most preferably between approximately 1 to 10 mg/kg/day, is generally sufficient.

The formulations include those suitable for oral, rectal, ophthalmic, (including intravitreal or intracameral) nasal, topical (including buccal and sublingual), vaginal or parenteral (including subcutaneous, intramuscular, intravenous, intradermal, intratracheal, and epidural) administration. The formulations may conveniently be presented in unit dosage form and may be prepared by conventional pharmaceutical techniques. Such techniques include the step of bringing into association the active ingredient and the pharmaceutical carrier(s) or excipient(s). In general, the formulations are prepared by uniformly and intimately bringing into associate the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil emulsion and as a bolus, etc.

A tablet may be made by compression or molding, optionally with one or more accessory ingredients. Compressed tablets may be prepared by compressing, in a suitable machine, the active ingredient in a free-flowing form such as a powder or granules, optionally mixed with a binder, lubricant, inert diluent, preservative, surface active or dispersing agent. Molded tablets may be made by molding, in a suitable machine, a mixture of the powdered compound moistened with an inert liquid diluent. The tablets may be optionally coated or scored and may be formulated so as to provide a slow or controlled release of the active ingredient therein.

Formulations suitable for topical administration in the mouth include lozenges comprising the ingredients in a flavored basis, usually sucrose and acacia or tragacanth; pastilles comprising the active ingredient in an inert basis such as gelatin and glycerin, or sucrose and acacia; and mouthwashes comprising the ingredient to be administered in a suitable liquid carrier.

Formulations suitable for topical administration to the skin may be presented as ointments, creams, gels and pastes comprising the ingredient to be administered in a pharmaceutical acceptable carrier. A preferred topical delivery system is a transdermal patch containing the ingredient to be administered.

Formulations for rectal administration may be presented as a suppository with a suitable base comprising, for example, cocoa butter or a salicylate.

Formulations suitable for nasal administration, wherein the carrier is a solid, include a coarse powder having a particle size, for example, in the range of 20 to 500 microns which is administered in the manner in which snuff is administered, i.e., by rapid inhalation through the nasal passage from a container of the powder held close up to the nose. Suitable formulations, wherein the carrier is a liquid, for administration, as for example, a nasal spray or as nasal drops, include aqueous or oily solutions of the active ingredient.

Formulations suitable for vaginal administration may be presented as pessaries, tamports, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) conditions requiring only the addition of the sterile liquid carrier, for example, water for injections, immediately prior to use. Extemporaneous injection solutions and suspensions may be prepared from sterile powders, granules and tablets of the kind previously described.

Preferred unit dosage formulations are those containing a daily dose or unit, daily sub-dose, as herein above recited, or an appropriate fraction thereof, of the administered ingredient.

It should be understood that in addition to the ingredients, particularly mentioned above, the formulations of the present invention may include other agents conventional in the art having regard to the type of formulation in question, for example, those suitable for oral administration may include flavoring agents.

Diseases associated with comeal neovascularization that can be treated according to the present invention include but are not limited to, diabetic retinopathy, retinopathy of prematurity, comeal graft rejection, neovascular glaucoma and retrolental fibroplasia, epidemic keratoconjunctivitis, Vitamin A deficiency, contact lens overwear, atopic keratitis, superior limbic keratitis, pterygium keratitis sicca, sjogrens, acne rosacea, phylectenulosis, syphilis, Mycobacteria infections, lipid degeneration, chemical burns, bacterial ulcers, fungal ulcers, *Herpes simplex* infections, *Herpes zoster* infections, protozoan infections, Kaposi sarcoma, Mooren ulcer, Terrien's marginal degeneration, mariginal keratolysis, trauma, rheumatoid arthritis, systemic lupus, polyarteritis, Wegeners sarcoidosis, Scleritis, Steven's Johnson disease, pemphigoid, radial keratotomy, and corneal graph rejection.

Diseases associated with retinal/choroidal neovascularization that can be treated according to the present invention include, but are not limited to, diabetic retinopathy, macular degeneration, sickle cell anemia, sarcoid, syphilis, pseudoxanthoma elasticum, Pagets disease, vein occlusion, artery occlusion, carotid obstructive disease, chronic uveitis/vitritis, mycobacterial infections, Lyme's disease, systemic lupus erythematosis, retinopathy of prematurity, Eales disease, Bechets disease, infections causing a retinitis or choroiditis, presumed ocular histoplasmosis, Bests disease, myopia, optic pits, Stargarts disease, pars planitis, chronic retinal detachment, hyperviscosity syndromes, toxoplasmosis, trauma and post-laser complications. Other diseases include, but are not limited to, diseases associated with rubeosis (neovasculariation of the angle) and diseases caused by the abnormal proliferation of fibrovascular or fibrous tissue including all forms of proliferative vitreoretinopathy, whether or not associated with diabetes.

Diseases associated with chronic inflammation can be treated by the compositions and methods of the present invention. Diseases with symptoms of chronic inflammation include inflammatory bowel diseases such as Crohn's disease and ulcerative colitis, psoriasis, sarcoidosis and rheumatoid arthritis. Angiogenesis is a key element that these chronic inflammatory diseases have in common. The chronic inflammation depends on continuous formation of capillary sprouts to maintain an influx of inflammatory cells. The influx and presence of the inflammatory cells produce granulomas and thus, maintains the chronic inflammatory state. Inhibition of angiogenesis by the compositions and methods of the present invention would prevent the formation of the granulomas and alleviate the disease.

The compositions and methods of the present invention can be used to treat patients with inflammatory bowel diseases such as Crohn's disease and ulcerative colitis. Both Crohn's disease and ulcerative colitis are characterized by chronic inflammation and angiogenesis at various sites in the gastrointestinal tract. Crohn's disease is characterized by chronic granulomatous inflammation throughout the gastrointestinal tract consisting of new capillary sprouts surrounded by a cylinder of inflammatory cells. Prevention of angiogenesis by the compositions and methods of the present invention inhibits the formation of the sprouts and prevents the formation of granulomas.

Crohn's disease occurs as a chronic transmural inflammatory disease that most commonly affects the distal ileum and colon but may also occur in any part of the gastrointestinal tract from the mouth to the anus and perianal area. Patients with Crohn's disease generally have chronic diarrhea associated with abdominal pain, fever, anorexia, weight loss and abdominal swelling. Ulcerative colitis is also a chronic, nonspecific, inflammatory and ulcerative disease arising in the colonic mucosa and is characterized by the presence of bloody diarrhea.

The inflammatory bowel diseases also show extraintestinal manifestations such as skin lesions. Such lesions are characterized by inflammation and angiogenesis and can occur at many sites other than the gastrointestinal tract. The compositions and methods of the present invention are also capable of treating these lesions by preventing the angiogenesis, thus reducing the influx of inflammatory cells and the lesion formation.

Sarcoidosis is another chronic inflammatory disease that is characterized as a multisystem granulomatous disorder. The granulomas of this disease may form anywhere in the body and thus the symptoms depend on the site of the granulomas and whether the disease active. The granulomas are created by the angiogenic capillary sprouts providing a constant supply of inflammatory cells.

The compositions and methods of the present invention can also treat the chronic inflammatory conditions associated with psoriasis. Psoriasis, a skin disease, is another chronic and recurrent disease that is characterized by papules and plaques of various sizes. Prevention of the formation of the new blood vessels necessary to maintain the characteristic lesions leads to relief from the symptoms.

Another disease which can be treated according to the present invention is rheumatoid arthritis. It is believed that the blood vessels in the synovial lining of the joints undergo angiogenesis. In addition to forming new vascular networks, the endothelial cells release factors and reactive oxygen species that lead to pannus growth and cartilage destruction. The factors involved in angiogenesis may actively contribute to, and help maintain, the chronically inflamed state of rheumatoid arthritis.

Another disease that can be treated according to the present invention are hemangiomas, Osler-Weber-Rendu disease, or hereditary hemorrhagic telangiectasia, solid or blood borne tumors and acquired immune deficiency syndrome.

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description. herein, may suggest themselves to those skilled in the art without departing from the spirit of the present invention and/or the scope of the appended claims.

EXAMPLE I

The chick embryo chorioallantoic membrane assay described by Crum et al., Science 230:1375 et seq. (1985), is used to identify compounds that do not require further metabolic conversion. See also, U.S. Pat. No. 5,001,116, hereby incorporated by reference, which describes the CAM assay at col. 7 of the patent. Briefly, fertilized chick embryos are removed from their shell on day 3 or 4, and a methylcellulose disc containing the compound is implanted on the chorioallantoic membrane. The embryos are examined 48 hours later and, if a clear avascular zone appears around the methylcellulose disc, the diameter of that zone is measured.

EXAMPLE II
Rabbit Cornea Angiogenesis Assay

Pellets for implantation into rabbit corneas were made by mixing 110 μl of saline containing 12 μg of recombinant bFGF (Takeda Pharmaceuticals-Japan) with 40 mg of sucralfate (Bukh Meditec-Denmark); this suspension was added to 80 μl of 12% hydron (Interferon Sciences) in ethanol. 10 μl aliquots of this mixture was then pipetted onto teflon pegs and allowed to dry producing approximately 17 pellets. A pellet was implanted into corneal micropockets of each eye of an anesthetized female New Zealand white rabbit, 2 mm from the limbus followed by topical application of erythromycin ointment onto the surface of the cornea. The animals were fed daily from 2 days post-implantation by gastric lavage with either drug suspended in 0.5% carboxymethyl cellulose or 0.5% carboxymethyl cellulose alone. Thalidomide was purchased from Andrulus Pharmaceutical (Maryland) and the EM-12 and Supidimide were kindly provided by Grunenthal GMBH (Germany). The animals were examined with a slit lamp every other day in a masked manner by the same corneal specialist. The area of corneal neovascularization was determined by measuring with a reticule the vessel length (L) from the limbus and the number of clock hours (C) of limbus involved. A formula was used to determine the area of a circular band segment:

C/12 * 3.1416 $[r^2-(r-L)^2]$ where r=6 mm the measured radius of the rabbit cornea. Various mathematical models were utilized to determine the amount of vascularized cornea and this formula was found to provide the most accurate approximation of the area of the band of neovascularization that grows towards the pellet.

It is important to note that the rabbit cornea assay is preferable because it will generally recognize compounds that are inactive per se but are metabolized to yield active compounds. Thalidomide related compounds, as shown below in Example III, are known to be teratogens and are candidates for use in the present invention.

EXAMPLE III

Inhibition of bFGF Induced Corneal Neovascularization by Thalidomide and Related Analog Expressed as Percent of Median Control on Day 8

Pellets containing bFGF and sucralfate were implanted into micropockets of both corneas of rabbits according to Example II. Vessel ingrowth into clear cornea from the limbus was first noted on day 2 and treatments (200 mg/kg orally) were begun on this day. The area of corneal neovascularization was measured from day 4 through day 12. Day 8 measurements were used for comparison between groups. No regression of vessels and near maximal neovascularization was seen at this time point. Statistical analysis was performed with ANOVA with ranked data to account for interexperimental. variation and to guard against a non-normal distribution of data (i.e. outliers) by utilizing a nonparametric method.

The compounds tested were as follows:

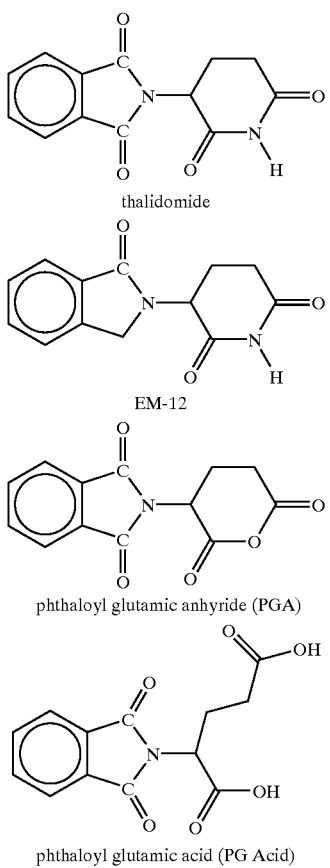

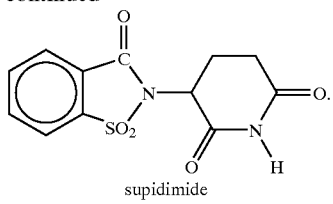

supidimide

Treatment with a dose of (200 mg/kg) of thalidomide resulted in an inhibition of the area of vascularized cornea that ranged from 30–51% in three experiments with a median inhibition of 36% (FIG. 6) (n=30 eyes, p=0.0001, 2 way ANOVA with ranked data). The inhibition of angiogenesis by thalidomide was seen after only two doses (FIG. 7). The rabbits did not demonstrate obvious sedation and there were no signs of toxicity or weight loss. The teratogenic analog EM-12, which shares the other properties of thalidomide was also inhibitory, with a median inhibition of 42% (n=10 eyes, p=0.002, 1-way ANOVA with ranked data). Supidimide, a nonteratogenic analog of thalidomide that retains the sedative properties of thalidomide, exhibited no activity (area 107% of control, n=10 eyes, not statistically different from control). Other analogs, PGA and PG acid displayed weaker inhibitory effects than thalidomide (data not shown). The density of vessel ingrowth in thalidomide-treated animals was also markedly reduced.

EXAMPLE IV

EM-12 in Rabbit Cornea Assay

EM-12 was tested in the rabbit cornea assay described in Example II at 100 mg/kg/day and showed 21% inhibition, and at 200 mg/kg/day the assay showed 43% inhibition.

EXAMPLE V

Phthaloyl Glutamic Acid in CAM

Phthaloyl glutamic acid was tested in the above described CAM assay and exhibit an avascular zone with a mild scar.

EXAMPLE VI

Phthaloyl Glutamic Acid in Rabbit Cornea Assay

Phthaloyl glutamic acid described above at 200 mg/kg and exhibited 29% inhibition of angiogenesis.

EXAMPLE VII

Phthaloyl Glutamic Anhydride in CAM Assay

Phthaloyl glutamic anhydride was test in the CAM assay described above and exhibited an avascular zone.

It should be understood, of course, that the foregoing relates only to preferred embodiments of the present invention and that numerous modifications or alterations may be made therein without departing from the spirit and the scope of the invention as set forth in the appended claims.

What is claimed is:

1. A compound selected from the group consisting of

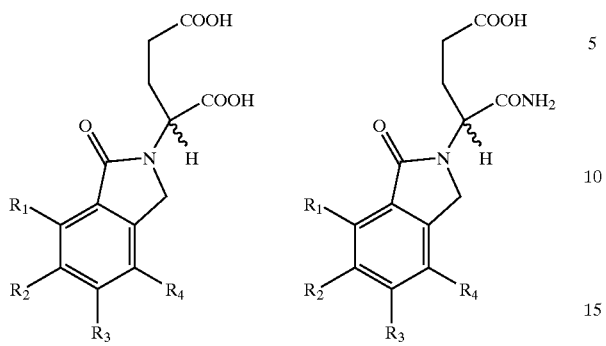

and

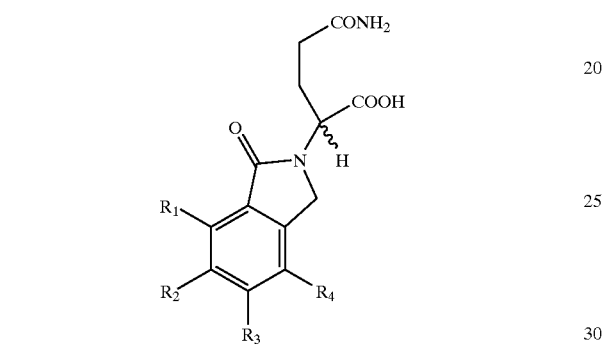

wherein $R_1$, $R_2$, $R_3$, and $R_4$ are independently selected from the group consisting of H and $NH_2$, with the proviso that at least one of $R_1$, $R_2$, $R_3$, and $R_4$ are $NH_2$.

2. The compound of claim 1 which is

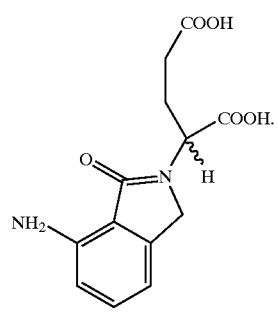

3. The compound of claim 1 which is

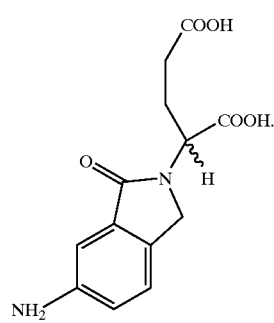

4. The compound of claim 1 which is

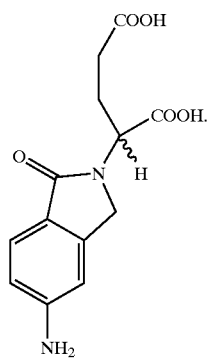

5. The compound of claim 1 which is

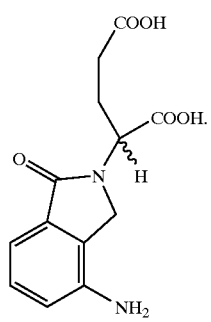

6. The compound of claim 1 which is

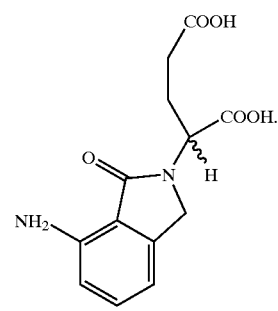

7. The compound of claim 1 which is

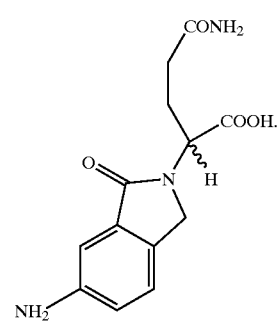

8. The compound of claim 1 which is

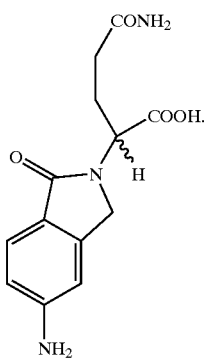

9. The compound of claim 1 which is

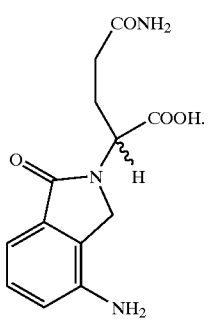

10. The compound of claim 1 which is

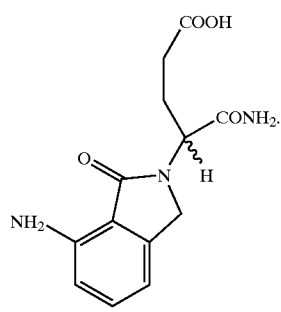

11. The compound of claim 1 which is

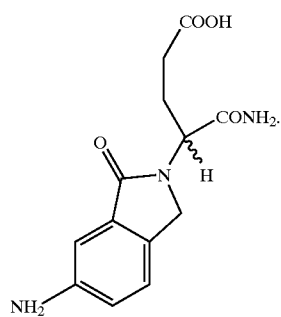

12. The compound of claim 1 which is

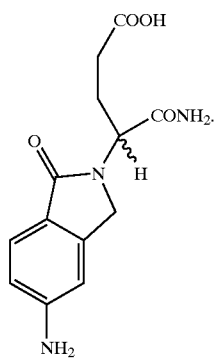

13. The compound of claim 1 which is

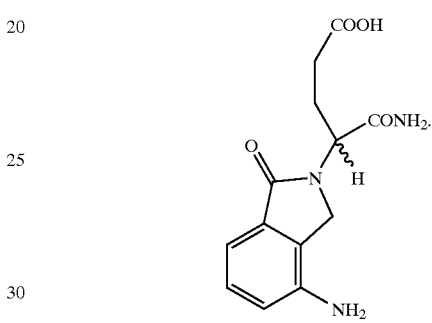

14. A composition comprising a compound according to claim 1 and a pharmaceutically acceptable carrier.

15. The composition of claim 14 wherein the compound is

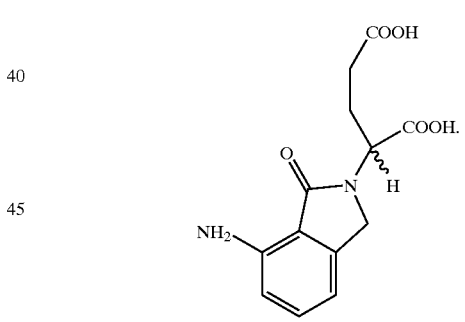

16. The composition of claim 14 wherein the compound is

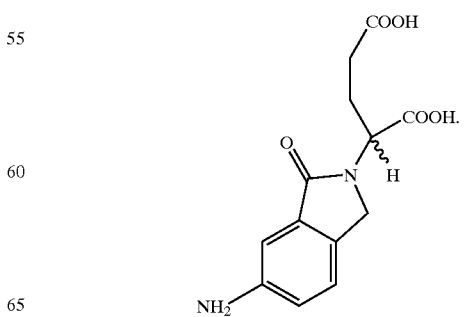

17. The composition of claim 14 wherein the compound is

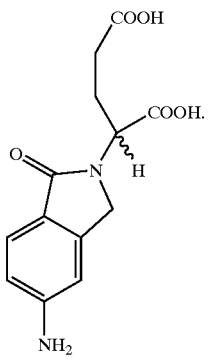

18. The composition of claim 14 wherein the compound is

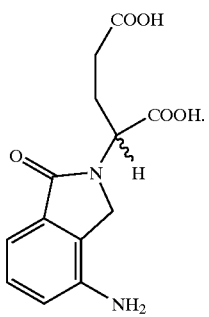

19. The composition of claim 14 wherein the compound is

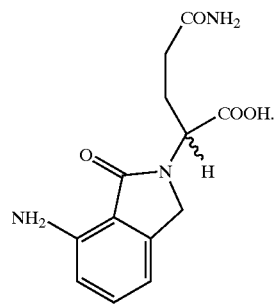

20. The composition of claim 14 wherein the compound is

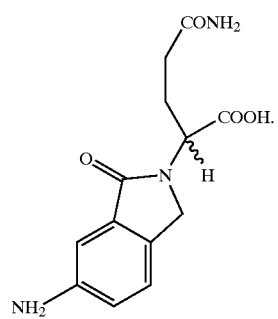

21. The composition of claim 14 wherein the compound is

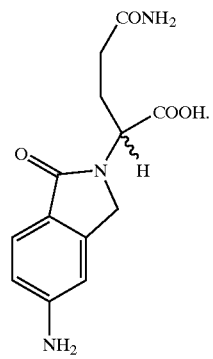

22. The composition of claim 14 wherein the compound is

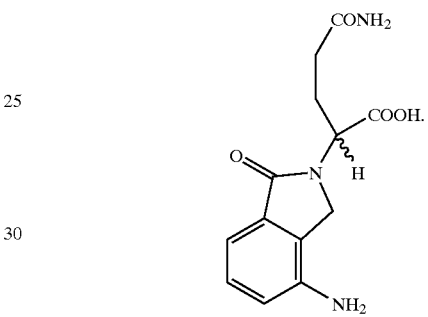

23. The composition of claim 14 wherein the compound is

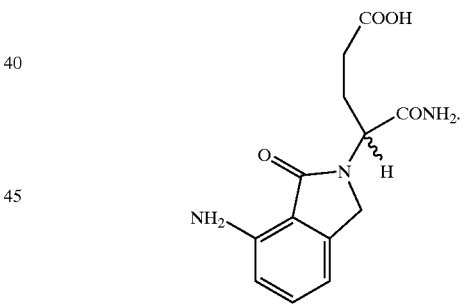

24. The composition of claim 14 wherein the compound is

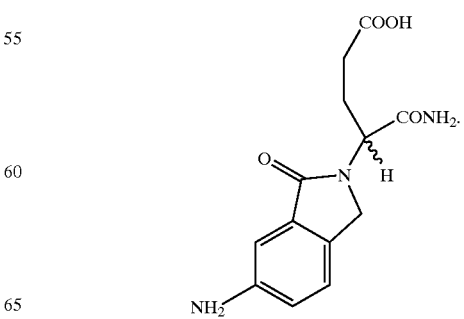

25. The composition of claim 14 wherein the compound is

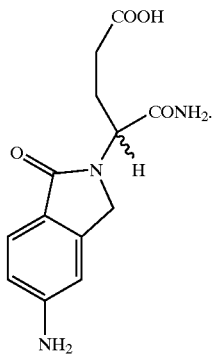

26. The composition of claim 14 wherein the compound is

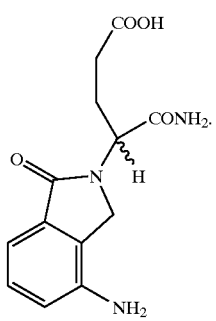

27. A method of inhibiting angiogenesis in a human or animal comprising administering to the human or animal an angiogenesis inhibiting amount of a compound of claim 1 or a pharmaceutical composition thereof.

28. The method of claim 27 wherein the compound is

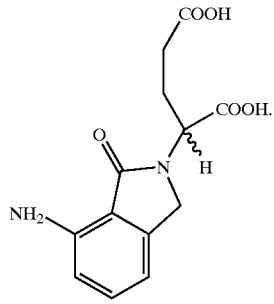

29. The method of claim 27 wherein the compound is

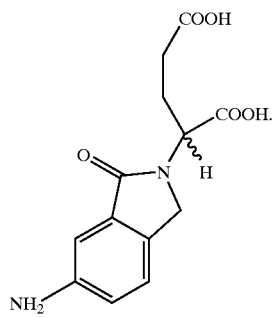

30. The method of claim 27 wherein the compound is

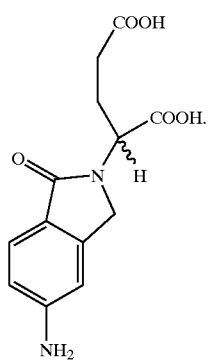

31. The method of claim 27 wherein the compound is

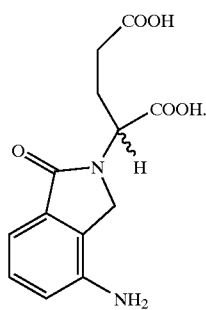

32. The method of claim 27 wherein the compound is

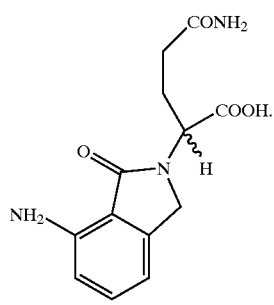

33. The method of claim 27 wherein the compound is

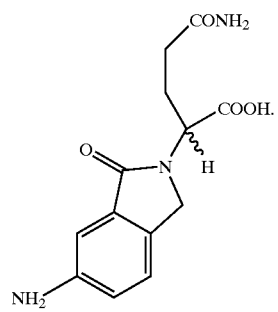

34. The method of claim 27 wherein the compound is

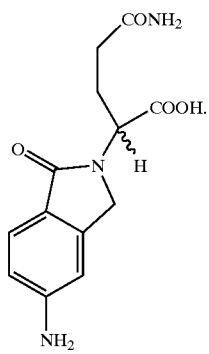

35. The method of claim 27 wherein the compound is

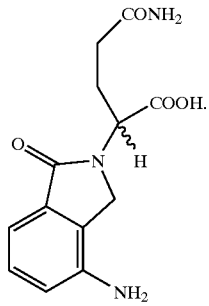

36. The method of claim 27 wherein the compound is

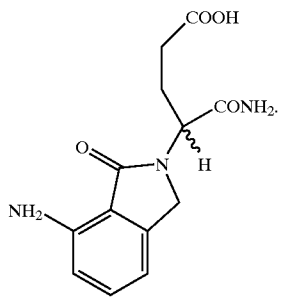

37. The method of claim 27 wherein the compound is

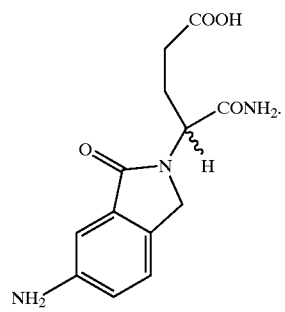

38. The method of claim 27 wherein the compound is

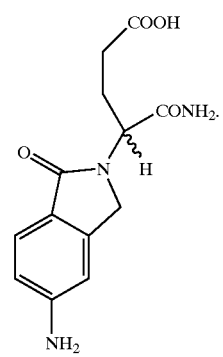

39. The method of claim 27 wherein the compound is

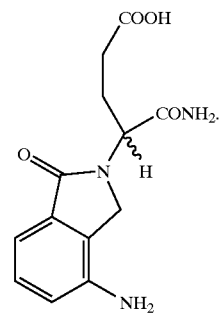

40. A method of treating an angiogenesis-dependent disease in a human or animal comprising administering to the human or animal an effective amount of a compound of claim 1 or a pharmaceutical composition thereof.

41. The method of claim 40 wherein the compound is

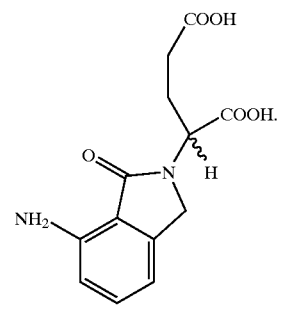

42. The method of claim 40 wherein the compound is
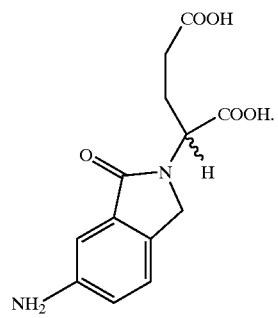
43. The method of claim 40 wherein the compound is
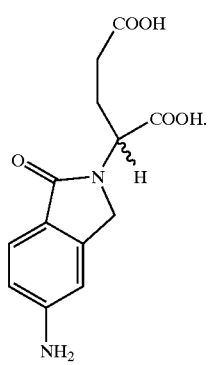
44. The method of claim 40 wherein the compound is
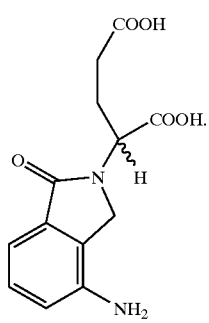
45. The method of claim 40 wherein the compound is
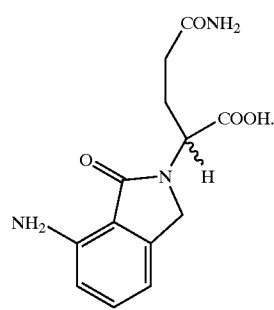
46. The method of claim 40 wherein the compound is
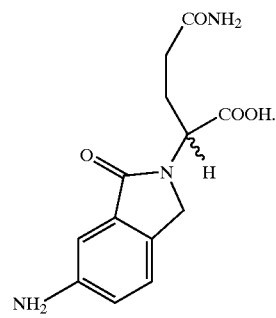
47. The method of claim 40 wherein the compound is
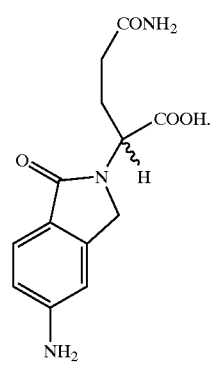
48. The method of claim 40 wherein the compound is
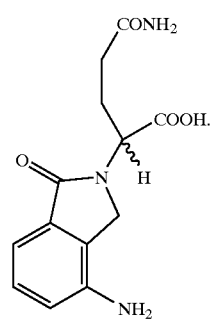
49. The method of claim 40 wherein the compound is
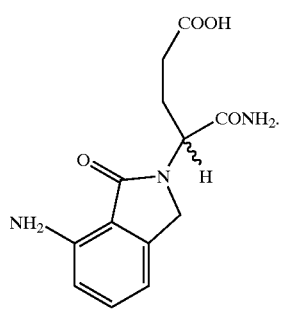

50. The method of claim 40 wherein the compound is
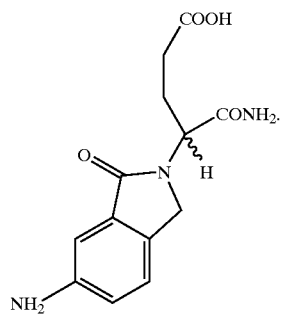
51. The method of claim 40 wherein the compound is
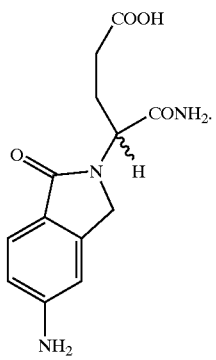
52. The method of claim 40 wherein the compound is
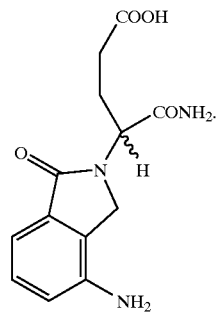
wherein each of $R_{12}$–$R_{17}$ is (independently) the same as defined above for $R_5$ and where $R_{11}$ is (independently) the same as defined above for $R_8$
In the above formula H), $R_{18}$, $R_{19}$, and $R_{20}$ are independently selected from
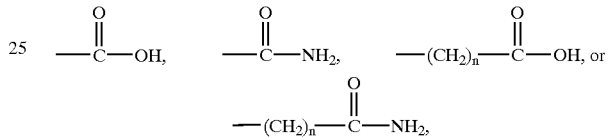
and n=1 to 4.
* * * * *